(12) United States Patent
Takada et al.

(10) Patent No.: US 8,889,268 B2
(45) Date of Patent: Nov. 18, 2014

(54) ORGANIC ELECTROLUMINESCENCE ELEMENT AND DISPLAY DEVICE USING THE SAME

(75) Inventors: Ichinori Takada, Kanagawa (JP);
Tadahiko Yoshinaga, Kanagawa (JP);
Emiko Kambe, Kanagawa (JP);
Shigeyuki Matsunami, Fukuoka (JP);
Yasunori Kijima, Tokyo (JP)

(73) Assignee: Sony Corporation, Tokyo (JP)

( * ) Notice: Subject to any disclaimer, the term of this patent is extended or adjusted under 35 U.S.C. 154(b) by 481 days.

(21) Appl. No.: 12/910,008

(22) Filed: Oct. 22, 2010

(65) Prior Publication Data
US 2011/0031877 A1 Feb. 10, 2011

(30) Foreign Application Priority Data
Oct. 29, 2009 (JP) .................... 2009-248573

(51) Int. Cl.
H01L 51/54 (2006.01)
C09K 11/06 (2006.01)
H01L 51/00 (2006.01)
C07F 7/08 (2006.01)
C07C 211/54 (2006.01)
H05B 33/14 (2006.01)
H05B 33/22 (2006.01)
H01L 51/50 (2006.01)

(52) U.S. Cl.
CPC .......... H01L 51/0059 (2013.01); C07F 7/0818 (2013.01); C07C 211/54 (2013.01); C09K 11/06 (2013.01); H05B 33/14 (2013.01); H05B 33/22 (2013.01); C09K 2211/1014 (2013.01); H01L 51/006 (2013.01); H01L 51/0085 (2013.01); H01L 51/5048 (2013.01); Y10S 428/917 (2013.01)
USPC ........... 428/690; 428/917; 313/504; 313/506; 252/301.16; 257/40; 257/103; 257/E51.05; 564/433

(58) Field of Classification Search
CPC ..... C07C 211/54; C07F 7/081; C07F 7/0818; H01L 51/0059; H01L 51/006; H01L 51/5048; H01L 51/5052; H01L 51/5056; H01L 51/506; C09K 11/06; C09K 2211/1014
See application file for complete search history.

(56) References Cited

U.S. PATENT DOCUMENTS

2002/0094452 A1* 7/2002 Ueda et al. .................... 428/690
2010/0171080 A1 7/2010 Kusano et al.

FOREIGN PATENT DOCUMENTS

JP 2006-352088 12/2006
WO 2005/063684 7/2005

OTHER PUBLICATIONS

Tong et al. "High Tg triphenylamine-based starburst hole-transporting material for organic light-emitting devices." Chem Mater. 2007, vol. 19, No. 24, pp. 5851-5855.*

Yasuhiko Shirota and Hiroshi Kageyama; Charge Carrier Transporting Molecular Materials and Their Applications in Devices; Chem. Rev. 2007; 207, 953-1010.

* cited by examiner

Primary Examiner — Michael H Wilson
(74) Attorney, Agent, or Firm — Dentons US LLP

(57) ABSTRACT

An organic electroluminescence element that includes a pair of electrodes and an organic light emitting functional layer. The organic light emitting functional layer being a multilayer structure made of an organic material between the pair of electrodes, and containing at least one of a material represented by the general formula (1), and a material represented by the general formula (2) in the multilayer structure, where general formula (1) and general formula (2) are:

the general formula (1)

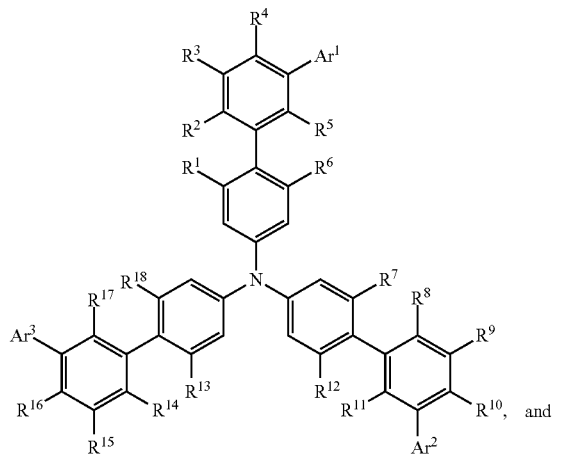

and the general formula (2)

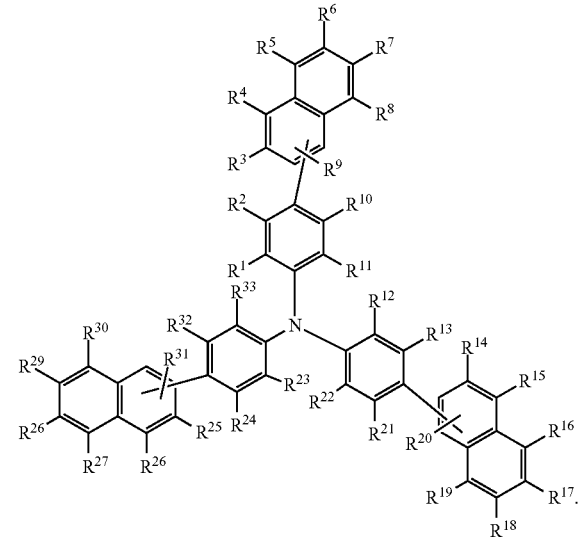

$$\begin{bmatrix} R^9 = \beta H, R^4 = H \\ R^{20} = \beta H, R^{15} = H \\ R^{31} = \beta H, R^{26} = H \end{bmatrix}$$

6 Claims, 6 Drawing Sheets

F I G . 3
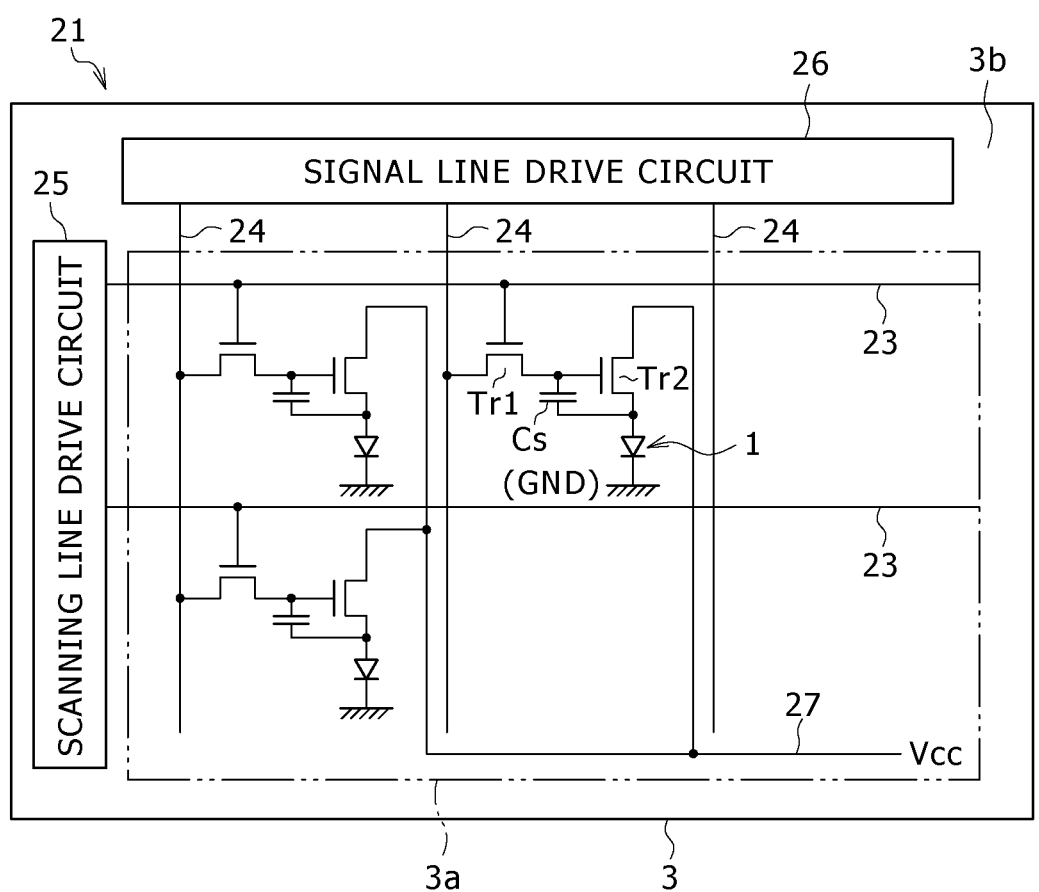

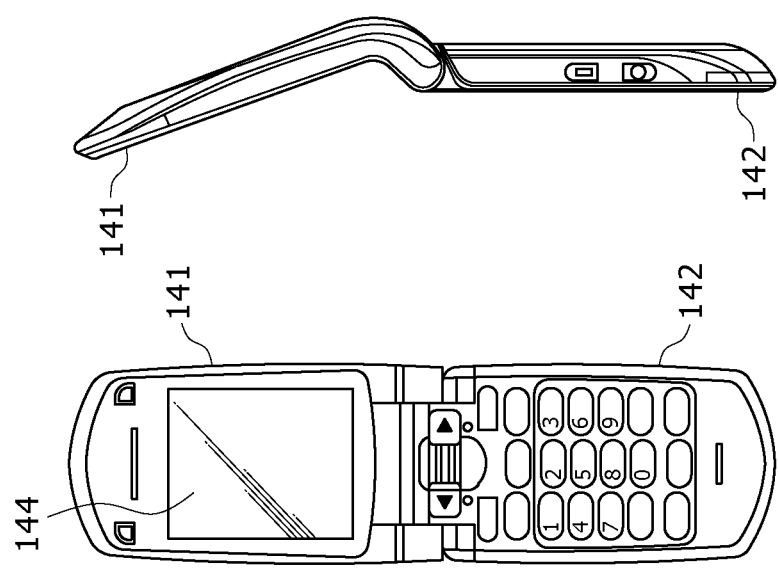
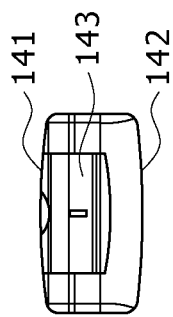
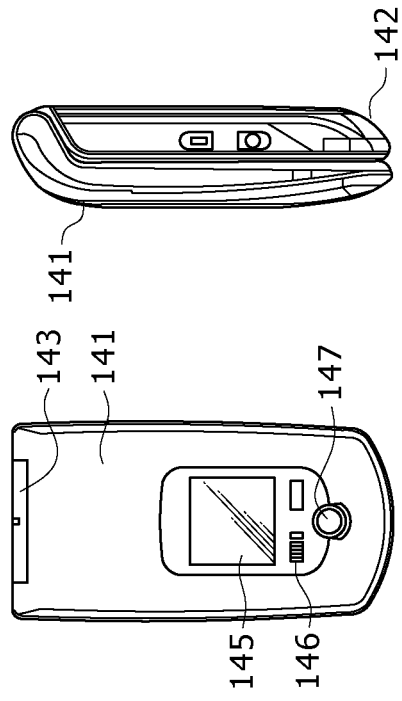
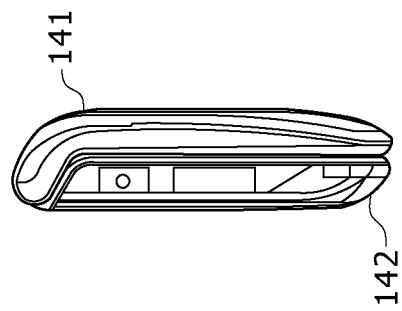
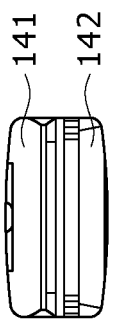
FIG. 9A  FIG. 9B  FIG. 9C  FIG. 9D  FIG. 9E  FIG. 9F  FIG. 9G

ORGANIC ELECTROLUMINESCENCE ELEMENT AND DISPLAY DEVICE USING THE SAME

BACKGROUND OF THE INVENTION

1. Field of the Invention

The present invention relates to an organic electroluminescence element and a display device using the same, and more particularly to an organic electroluminescence element having an excellent heat resistance property, and a display device using the same.

2. Description of the Related Art

An organic electroluminescence element (so-called organic EL element) utilizing electroluminescence of an organic material is provided with an organic light emitting functional layer including a light emitting layer between an anode and a cathode, and is attracting attention as a light emitting element which can make high-luminance luminescence by low-voltage D.C. driving. In such an organic electroluminescence element, a multilayer structure in which materials divide various parts with a structure of an organic light emitting functional layer, respectively, is adopted, thereby dramatically enhancing the characteristics.

In addition, for the purpose of realizing an organic electroluminescence element having a long life, a high luminance, and a high efficiency, in particular, a structure in which a monoamine compound is contained in a hole transport layer is proposed. In this case, in the structure using several compounds, the long life promotion, the high luminance promotion and the high efficiency promotion at a room temperature are confirmed. This technique, for example, is disclosed in Japanese Patent Laid-Open No. 2006-352088.

SUMMARY OF THE INVENTION

Now, it is demanded for the organic electroluminescence element to sustain the high luminous efficiency for a long time even under the high temperature condition.

The present embodiment has been made in order to solve the problems described above, and it is therefore desirable to provide an organic electroluminescence element which can sustain a high luminous efficiency for a long time even under a high temperature condition, and a display device using the same.

In order to attain the desire described above, according to an embodiment of the present invention, there is provided an organic electroluminescence element including: a pair of electrodes; and an organic light emitting functional layer structured as a multilayer structure made of an organic material held between the pair of electrodes, and containing at least one of a material represented by the general formula (1), and a material represented by the general formula (2) in the multilayer structure:

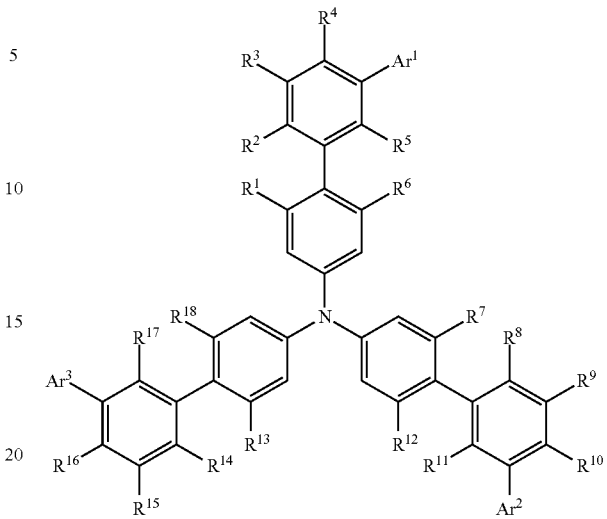

the general formula (1)

in which $Ar^1$ to $Ar^3$ are substituent groups which are selected from a phenyl group, a naphthyl group, a phenanthrenyl group, and an anthracenyl group and for which either an alkyl group having a carbon number of 6 or less or an organic compound group of 14-th group elements each heavier than carbon is adapted to be substituted, and $R^1$ to $R^{18}$ are hydrogen, an alkyl group having a carbon number of 6 or less or a phenyl group for which the alkyl group having the carbon number of 6 or less is adapted to be substituted, but at least one of the substituent groups of $R^2$ and $R^5$, and $R^8$ and $R^{11}$ is a substituent group other than hydrogen;

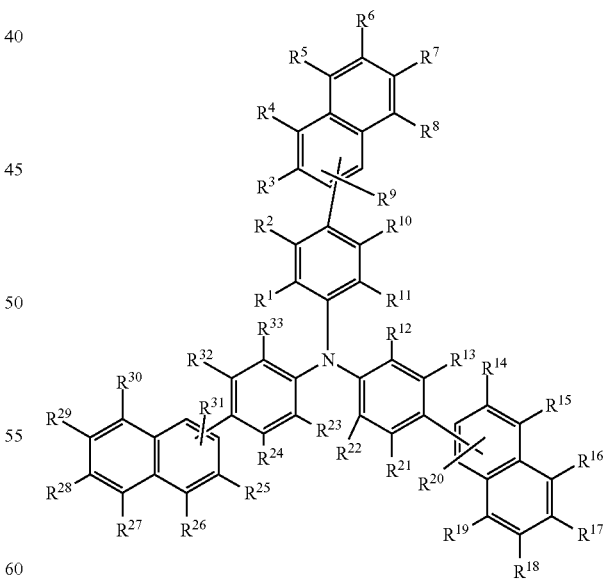

the general formula (2)

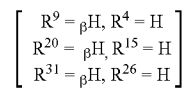

in which $R^1$ to $R^{33}$ are substituent groups which are selected from hydrogen, the alkyl group having the carbon number of 6 or less, and a phenyl group, a naphthyl group, a phenanthrenyl group, and an anthracenyl group for which either an alkyl group having a carbon number of 6 or less or an organic compound group of 14-th group elements each heavier than carbon is adapted to be substituted.

Compounds represented by the following structural formulas (1)-1 to (1)-41 are exemplified as concrete examples of the general formula (1) as shown above:

the structural formula (1)-1

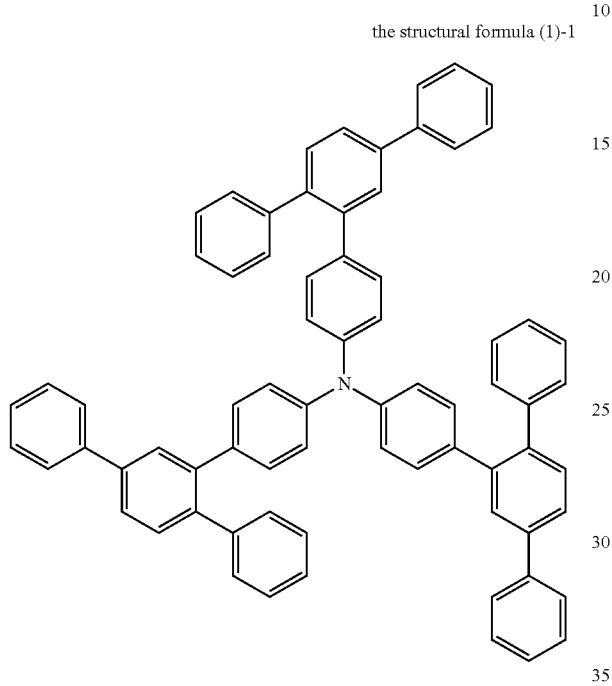

the structural formula (1)-2

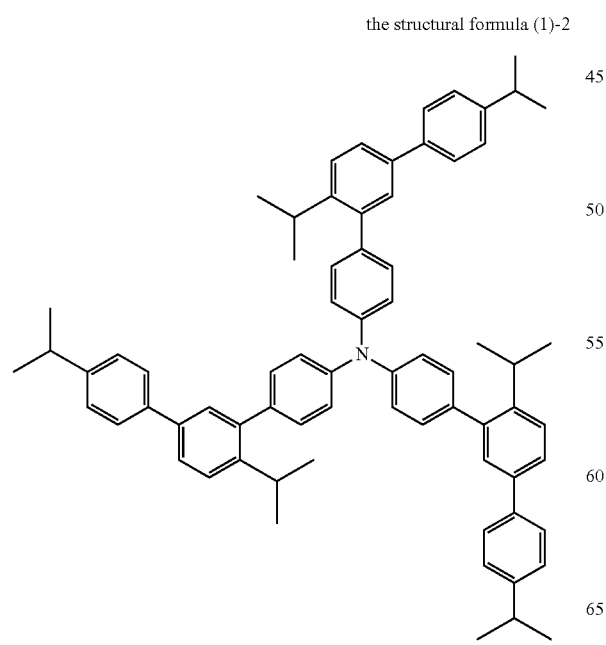

the structural formula (1)-3

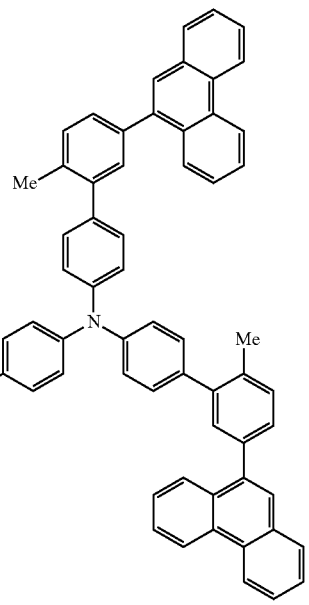

the structural formula (1)-4

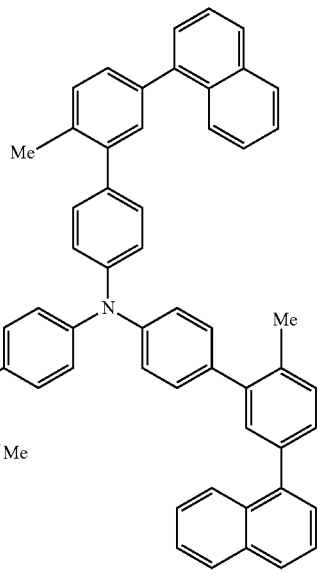

the structural formula (1)-5
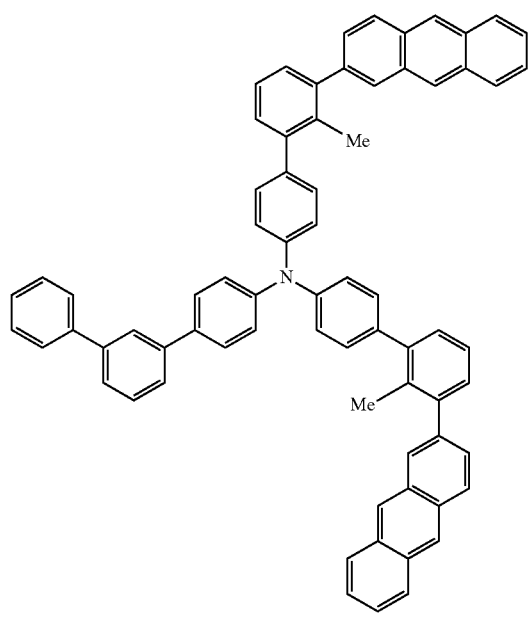
the structural formula (1)-6
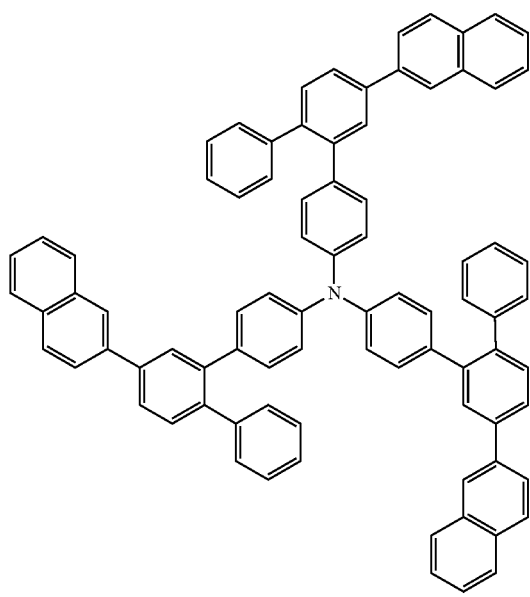
the structural formula (1)-7
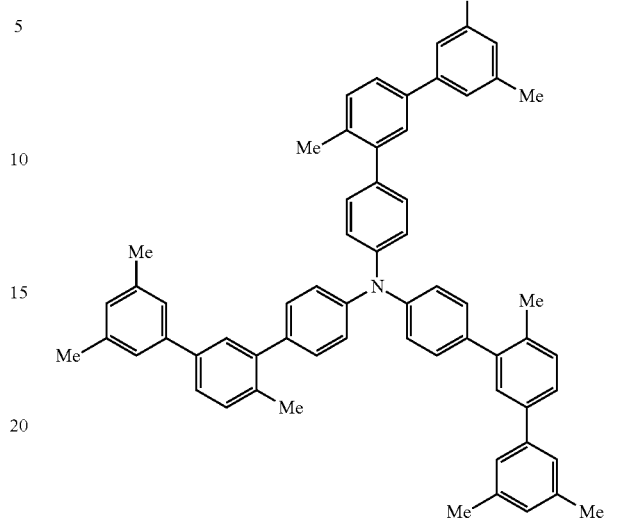
the structural formula (1)-8
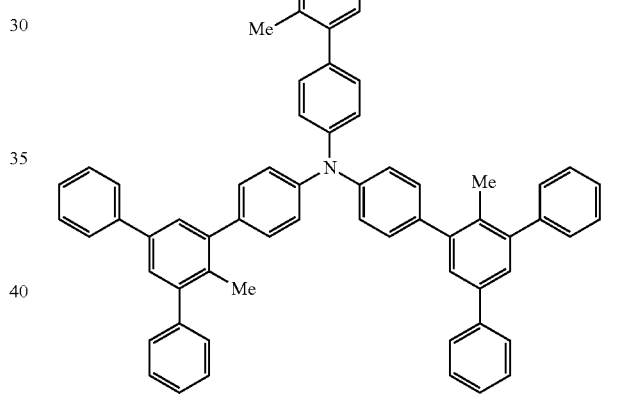
the structural formula (1)-9
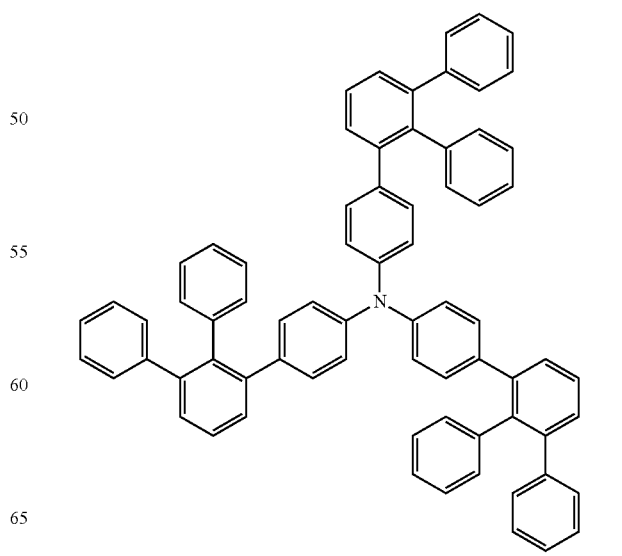

the structural formula (1)-10
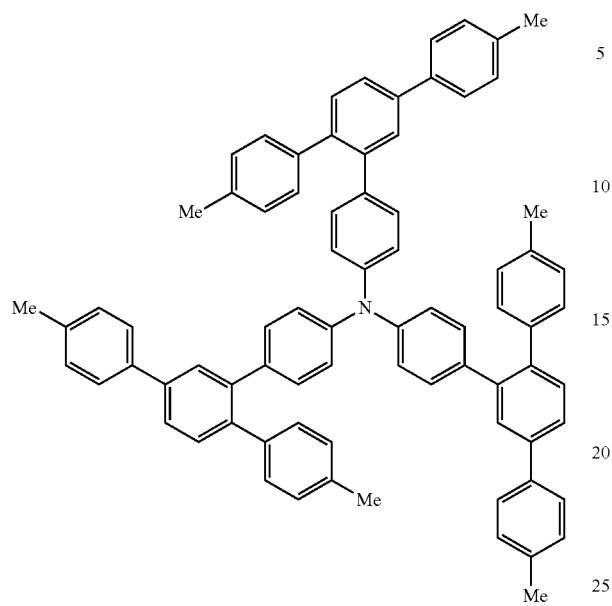
the structural formula (1)-12
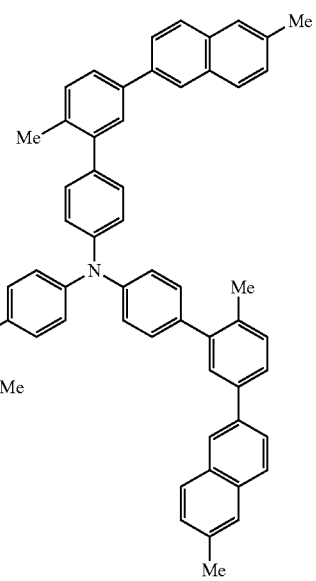
the structural formula (1)-11
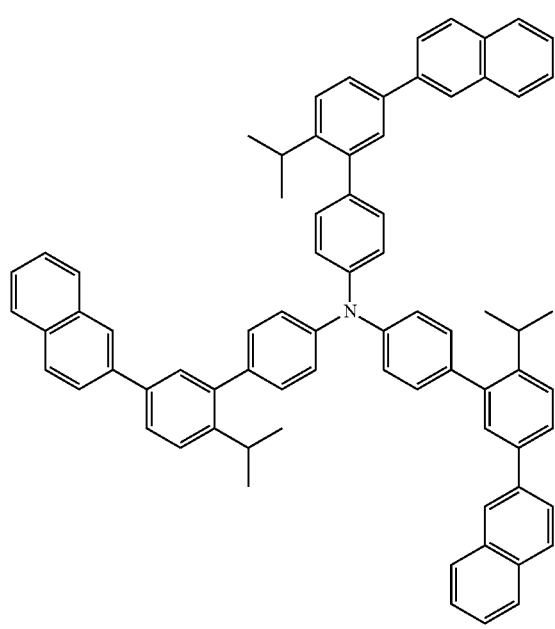
the structural formula (1)-13
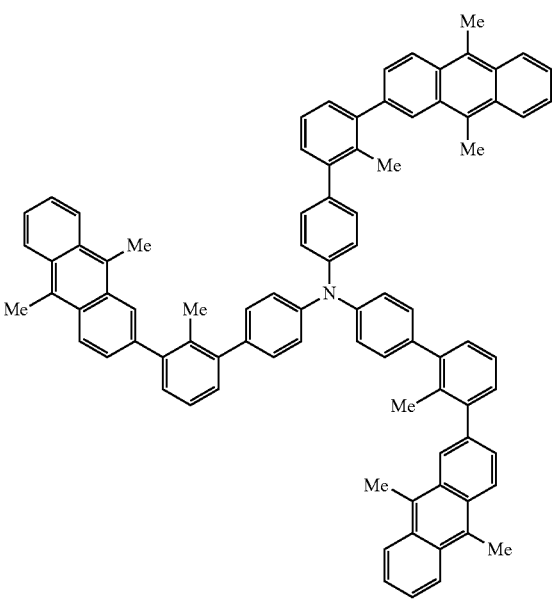

the structural formula (1)-14
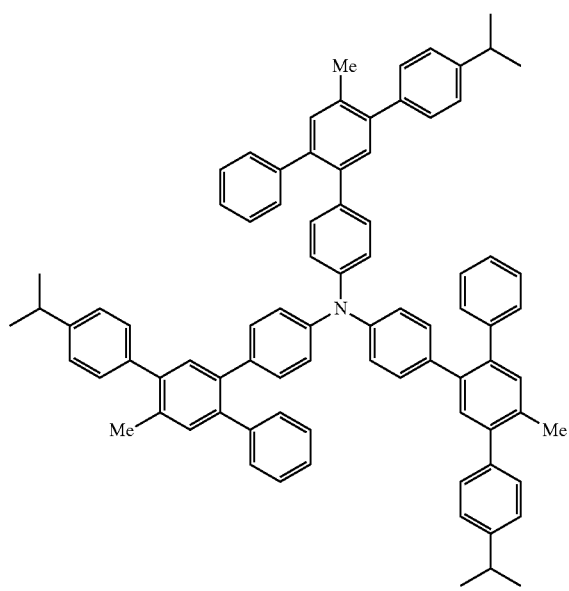
the structural formula (1)-15
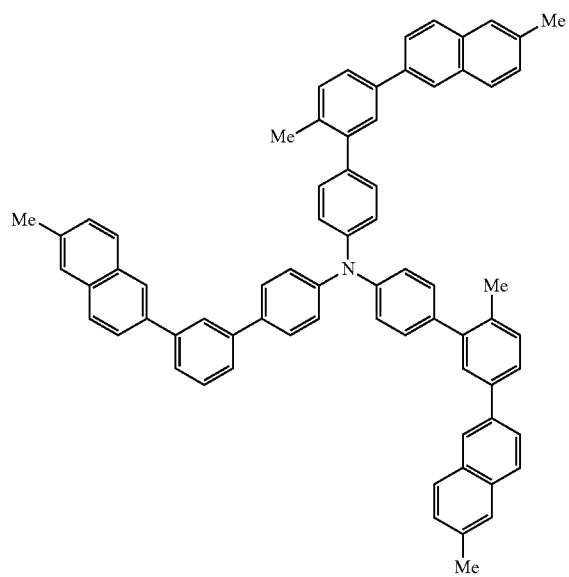
the structural formula (1)-16
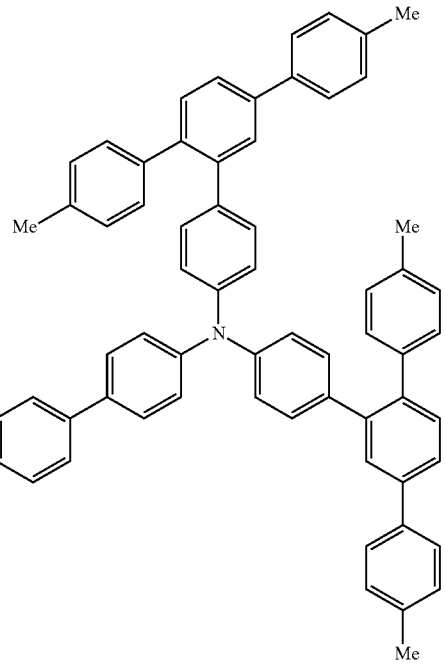
the structural formula (1)-17
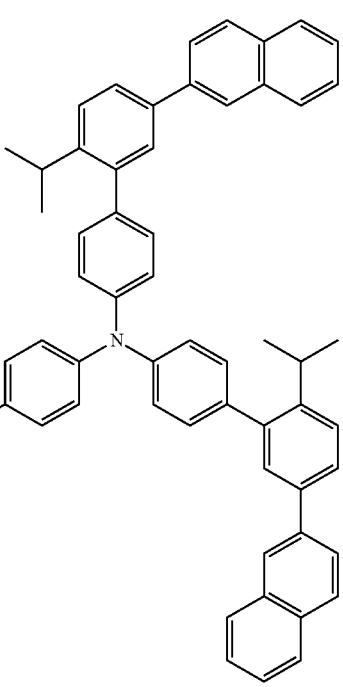

the structural formula (1)-18

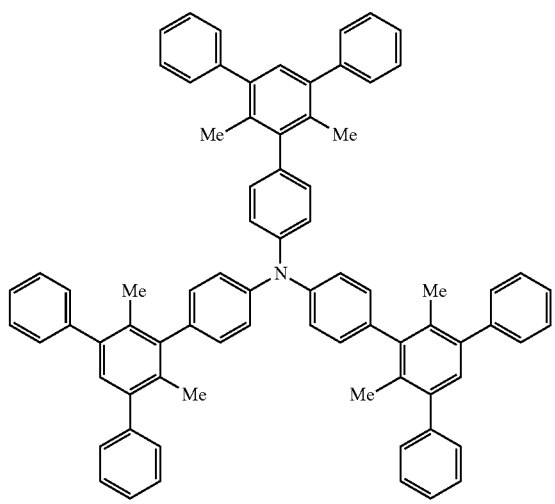

the structural formula (1)-19

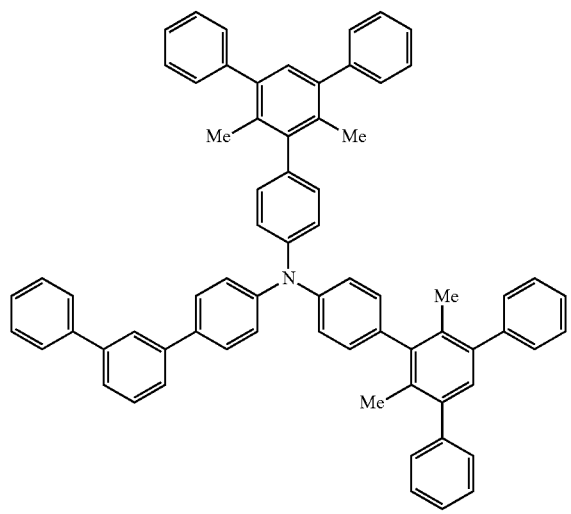

the structural formula (1)-20

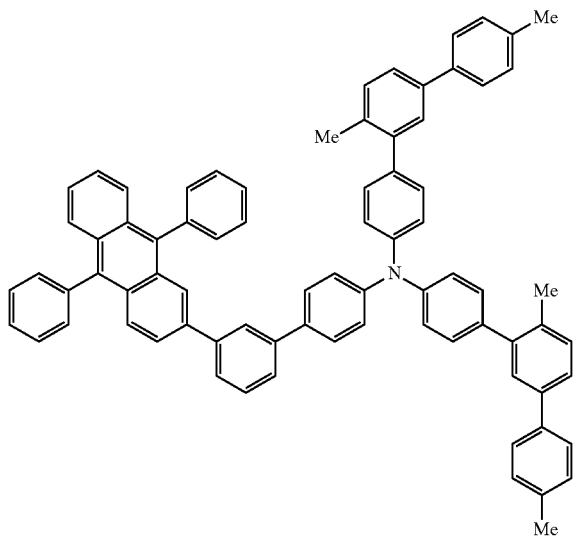

the structural formula (1)-21

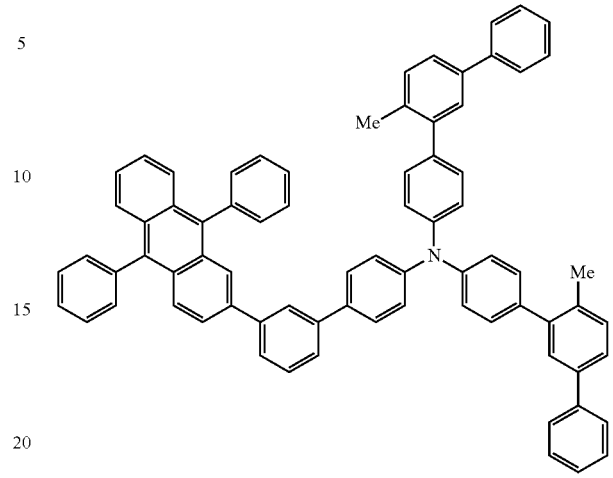

Firstly, the compounds represented by the structural formulas (1)-1 to (1)-21 are examples as the substituent groups which are selected from a phenyl group, a naphthyl group, a phenanthrenyl group, and an anthracenyl group, and in which the alkyl group having the carbon number of 6 or less may be substituted for $Ar^1$ to $Ar^3$ in the general formula (1).

Next, compounds represented by the structural formulas (1)-22 to (1)-41 are compounds having the phenyl group or the like in which the 14-th group elements each heavier than carbon are individually substituted for any ones of $Ar^1$ to $Ar^3$ in the general formula (1) as the substituent group. It is noted that the 14-th group element heavier than carbon is silicon (Si), germanium (Ge) or tin (Sn).

the structural formula (1)-22

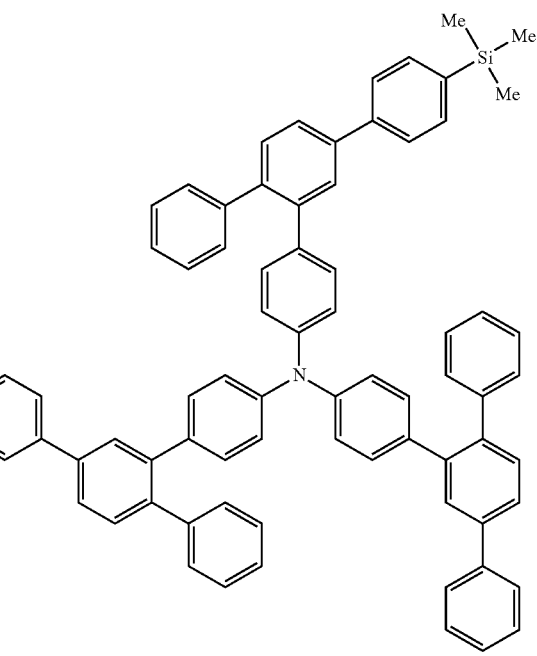

the structural formula (1)-23
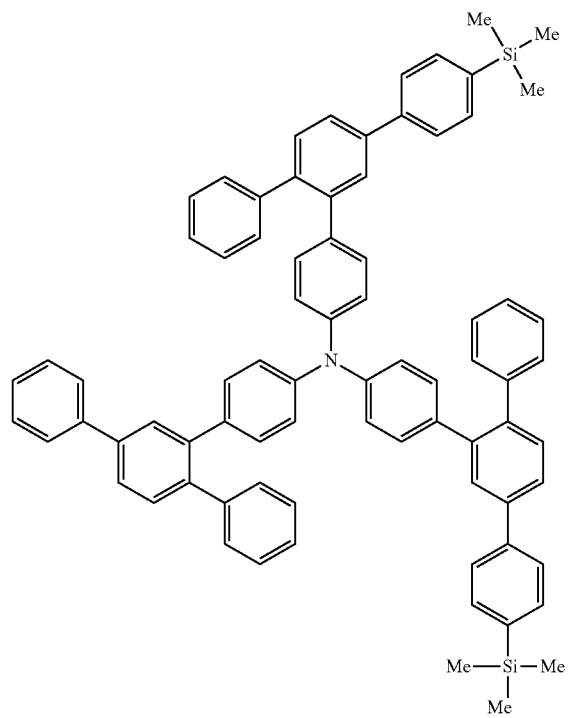
the structural formula (1)-24
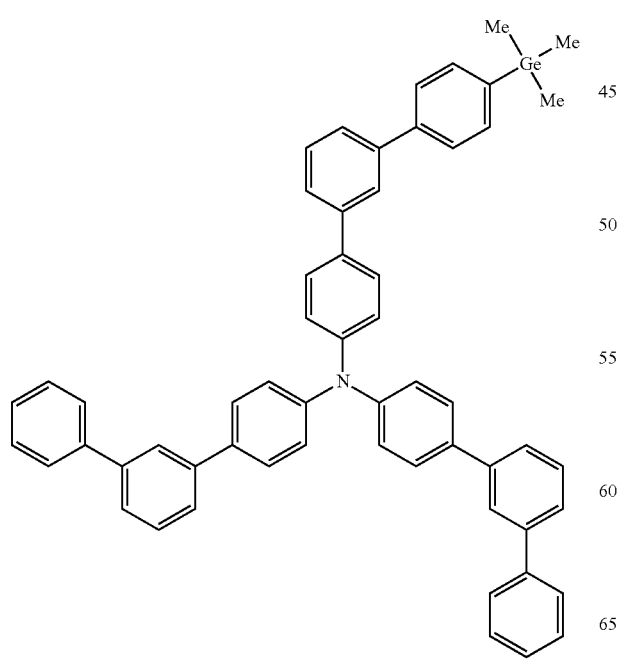
the structural formula (1)-25
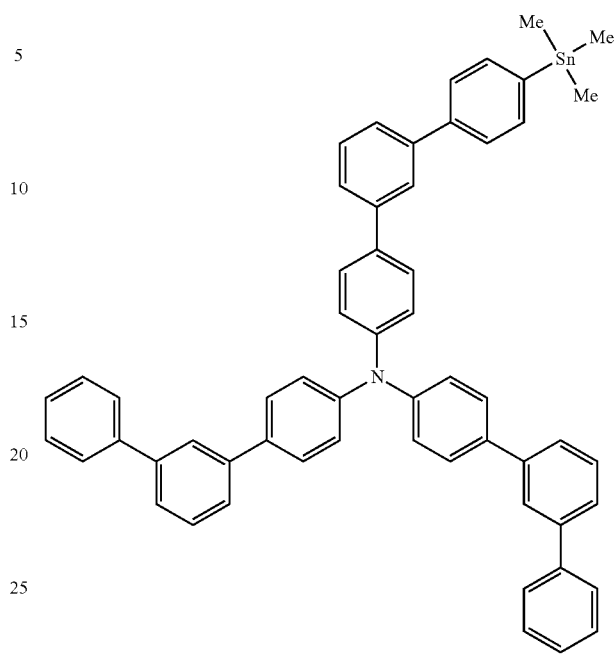
the structural formula (1)-26
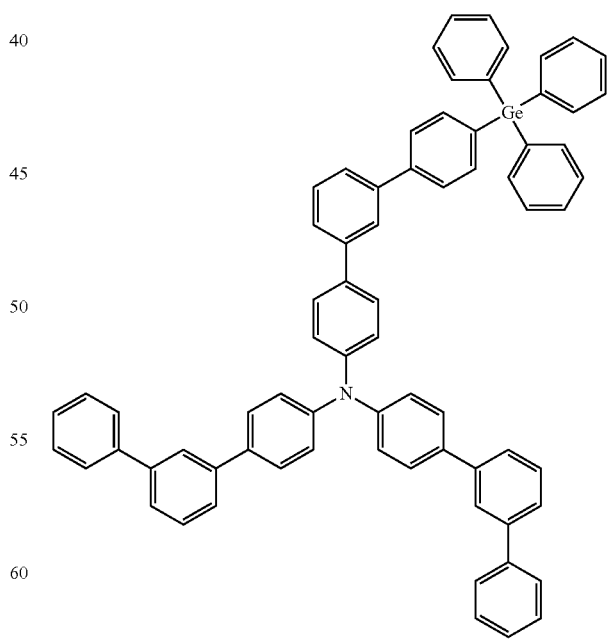

the structural formula (1)-27
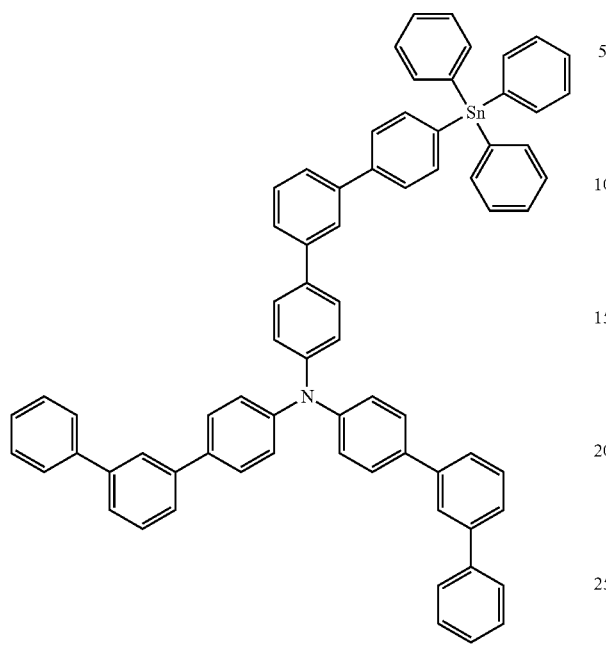
the structural formula (1)-29
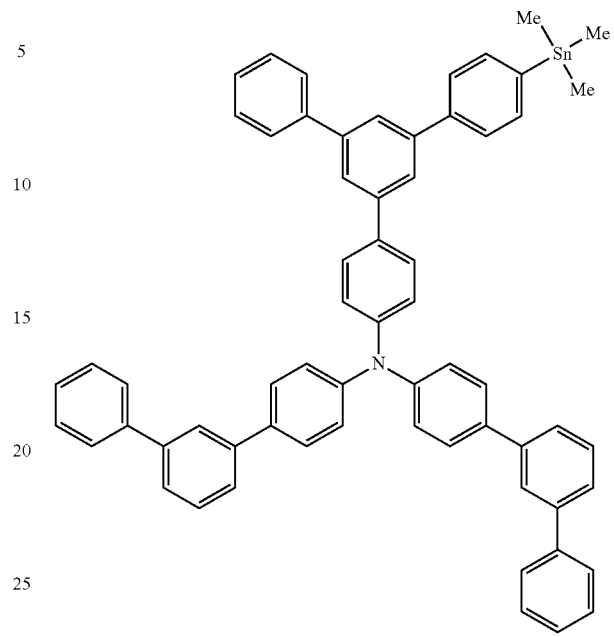
the structural formula (1)-28
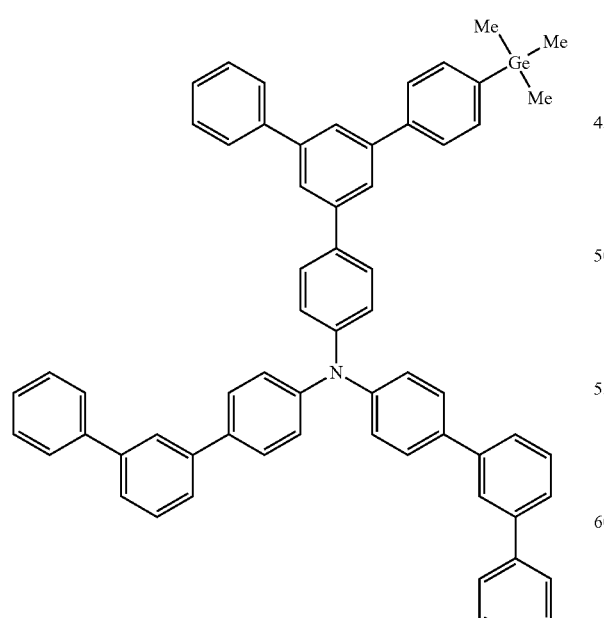
the structural formula (1)-30
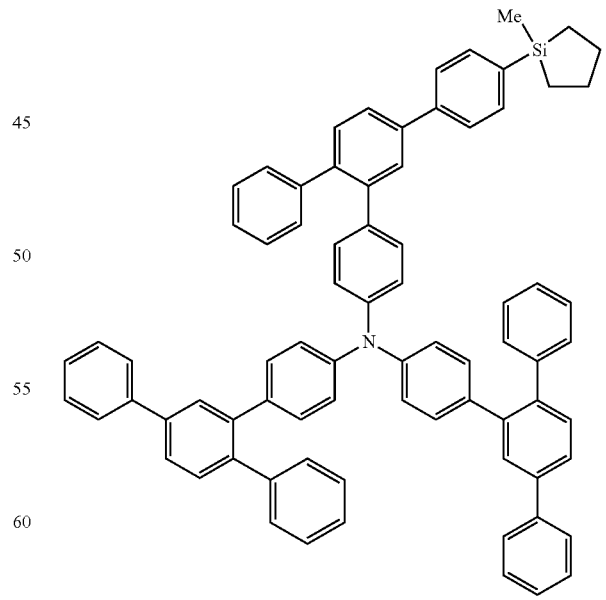

-continued
the structural formula (1)-31
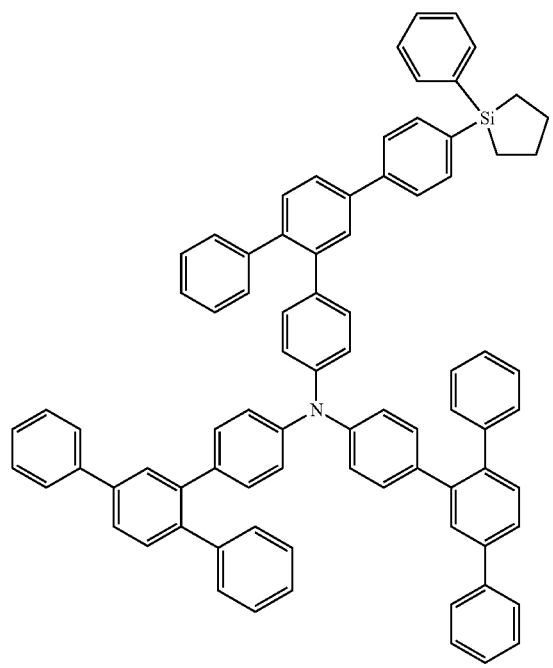
the structural formula (1)-32
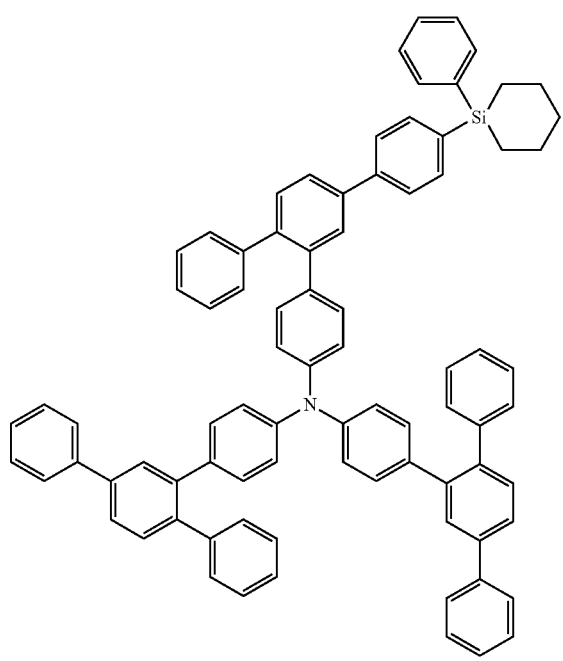
-continued
the structural formula (1)-33
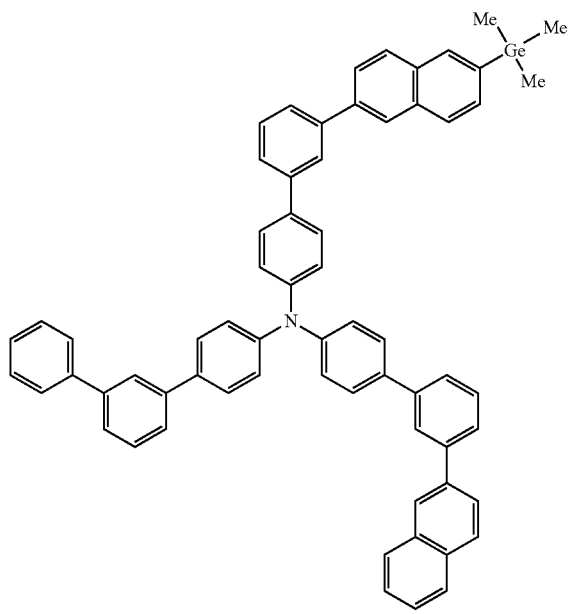
the structural formula (1)-34
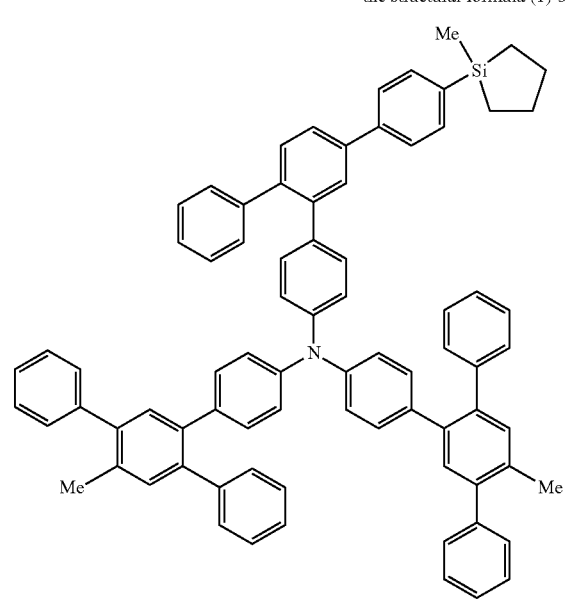

-continued
the structural formula (1)-35
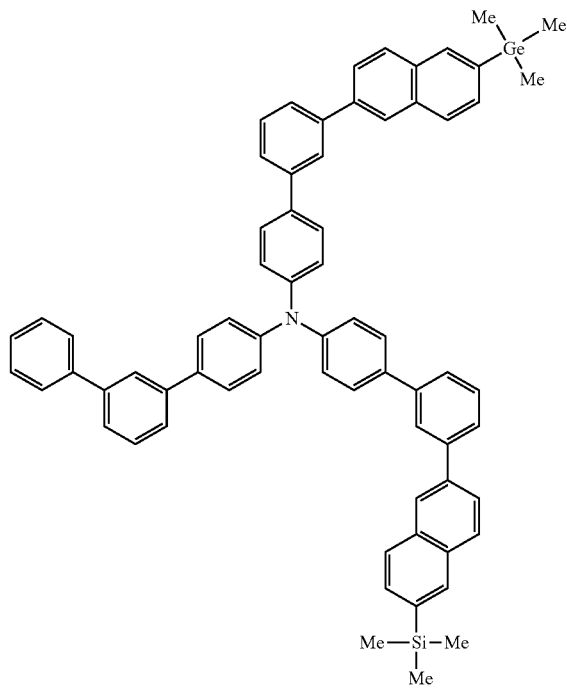
the structural formula (1)-36
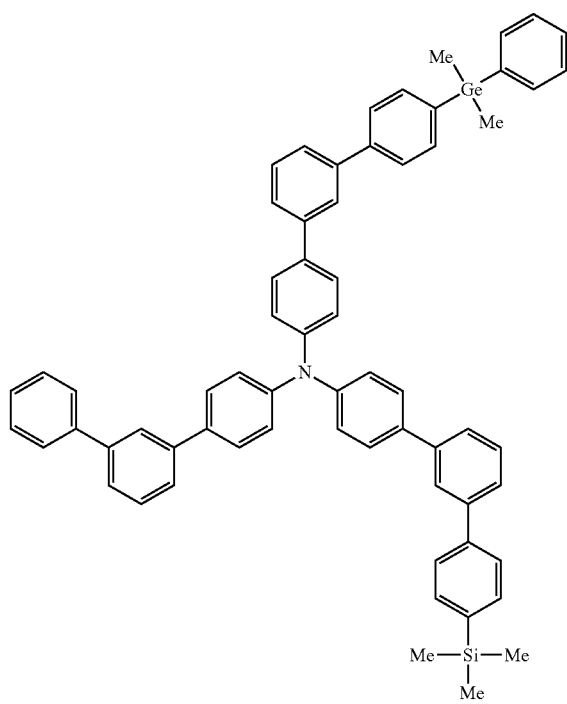
-continued
the structural formula (1)-37
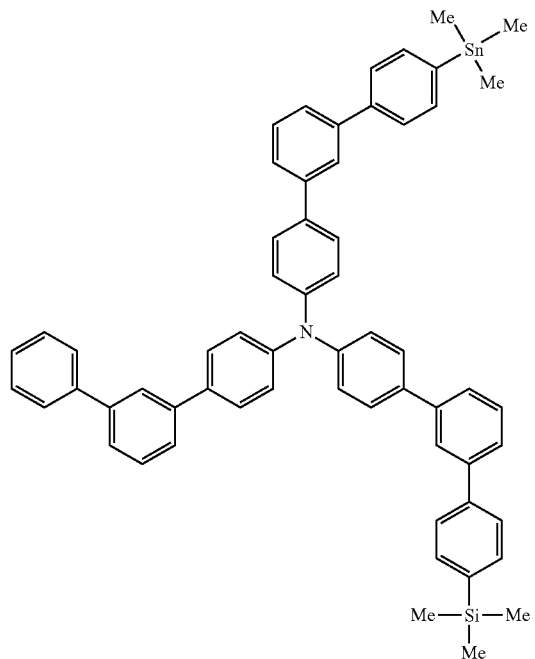
the structural formula (1)-38
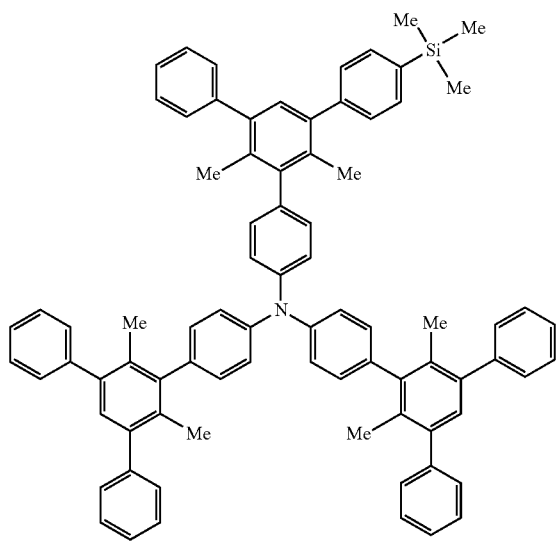

the structural formula (1)-39

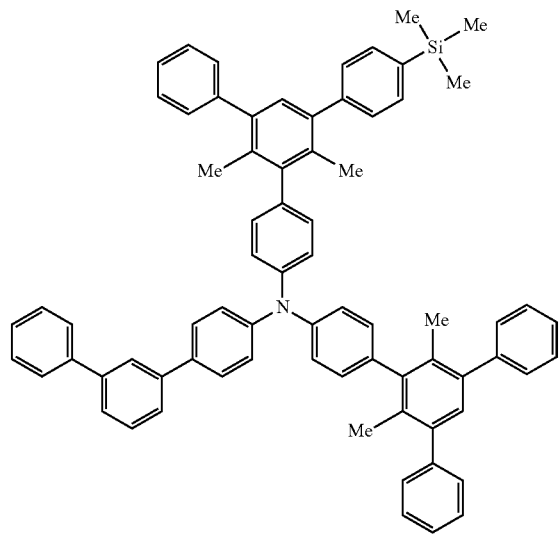

the structural formula (1)-41

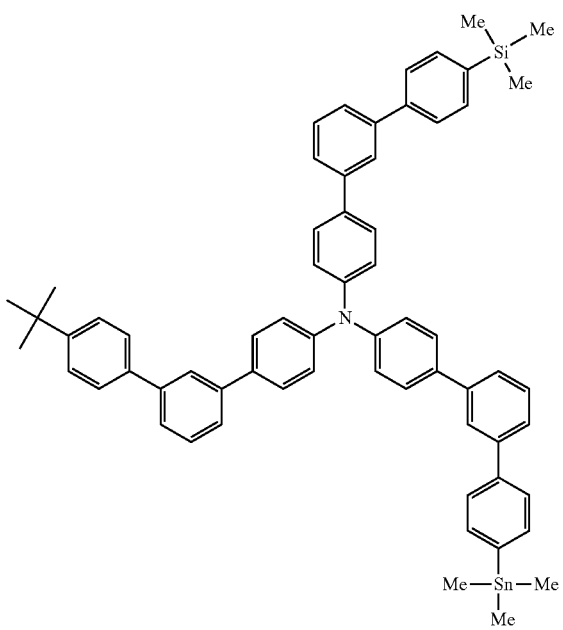

the structural formula (1)-40

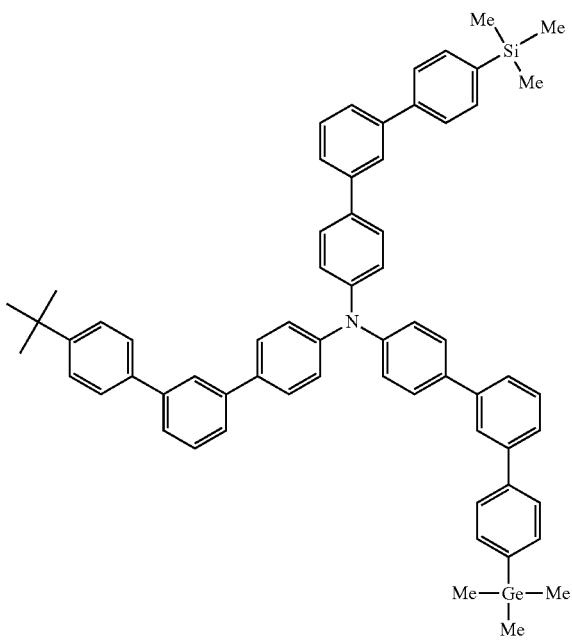

As described above, the organic compound group of the 14-th group elements each heavier than carbon represented in the general formula (1) has either the alkyl group having the carbon number of 6 or less or the phenyl group for which the alkyl group having the carbon number of 6 or less may be substituted. In addition, the groups bonded to the 14-th group elements each heavier than carbon may be linked to one another. In addition, when at least one of $Ar^1$ to $Ar^3$ or $R^1$ to $R^{18}$ is the substituent group for which the organic compound of the silicon element of the 14-th group elements is substituted, at least one of the substituent groups of $R^2$ and $R^5$, $R^8$ and $R^{11}$ is the substituent group other than hydrogen. In particular, preferably, in the substituent group for which the organic compound of the silicon element of the 14-th group elements is substituted, the substitution is made for at least one of $Ar^1$ to $Ar^3$.

In addition, compounds represented by the following structural formulas (2)-1 to (2)-37, respectively, are exemplified as concrete examples of the general formula (2) shown above:

the structural formula (2)-1
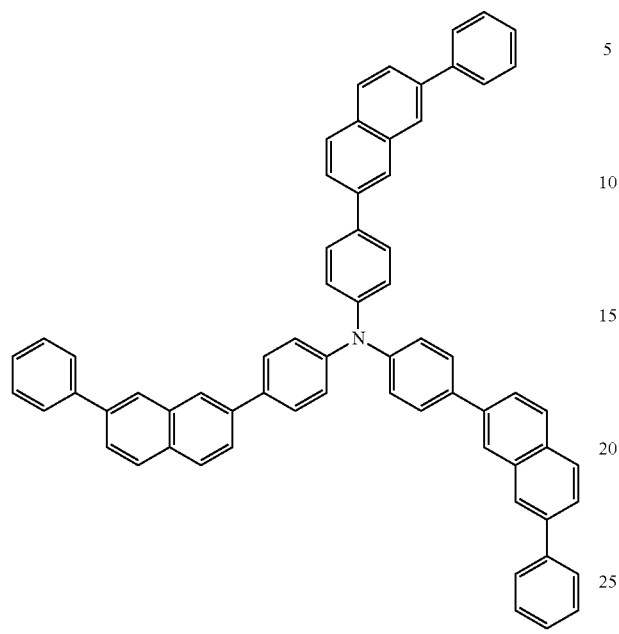
the structural formula (2)-3
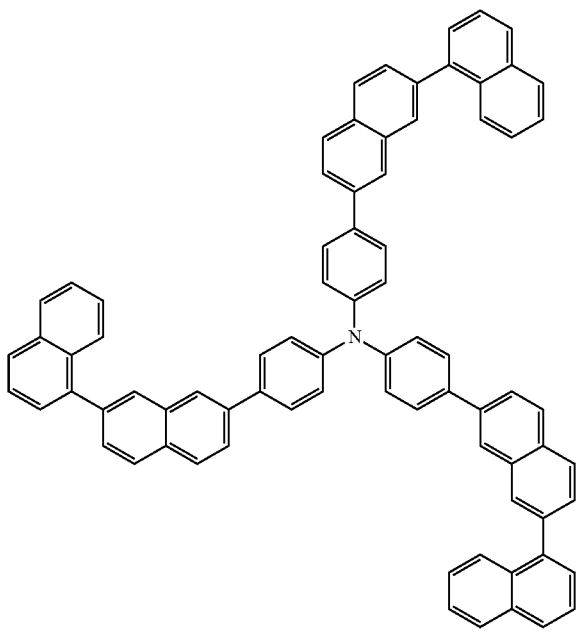
the structural formula (2)-2
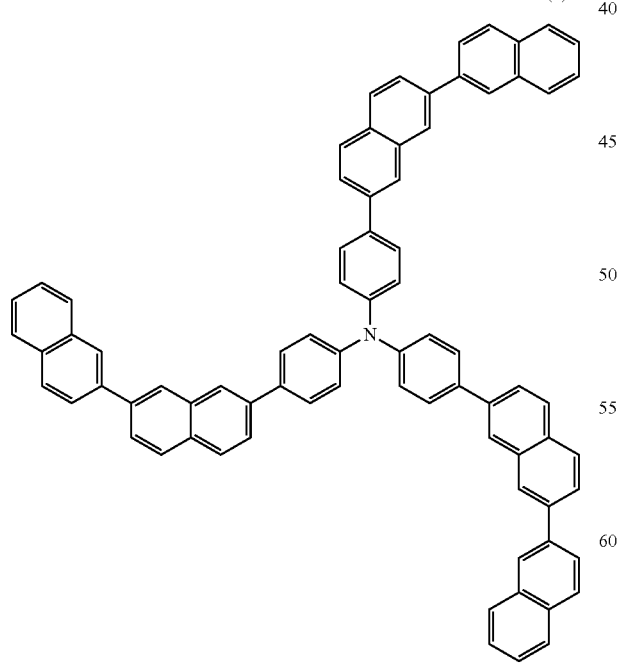
the structural formula (2)-4
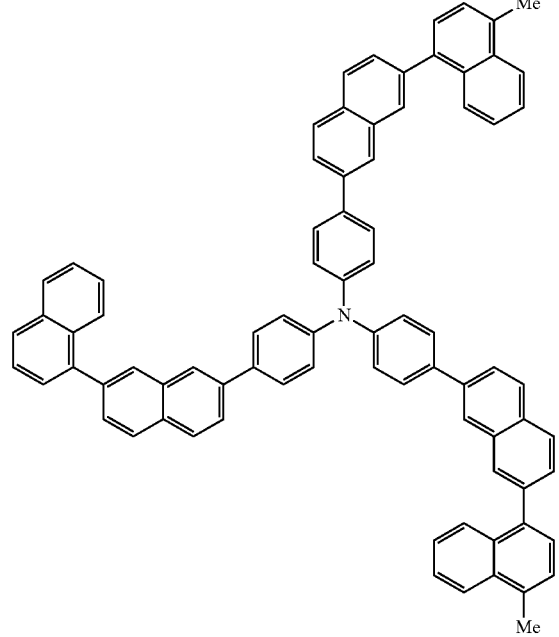

the structural formula (2)-5
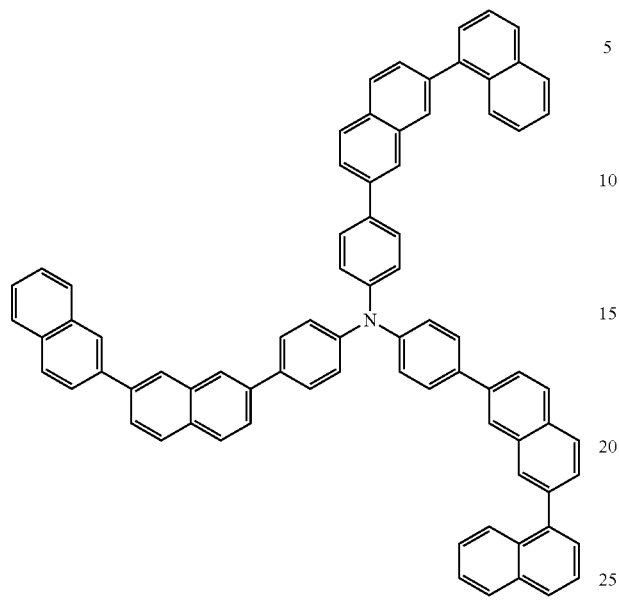
the structural formula (2)-7
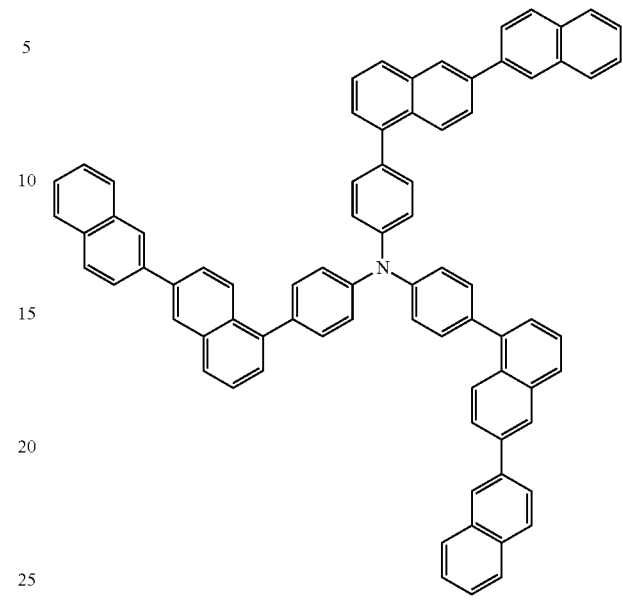
the structural formula (2)-6
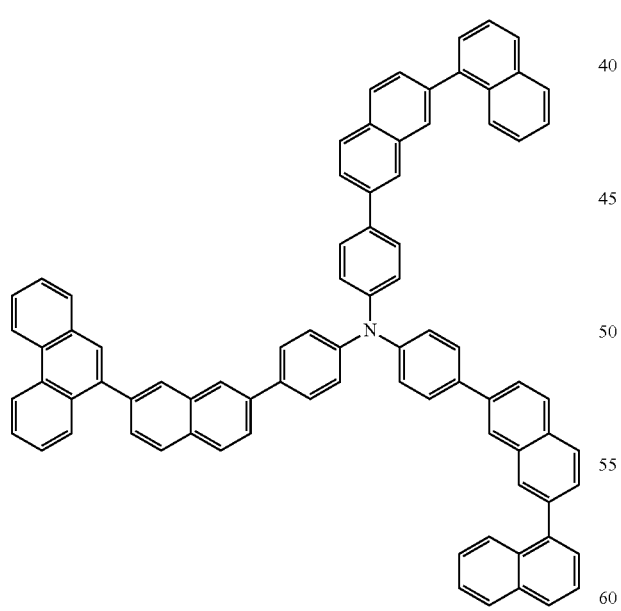
the structural formula (2)-8
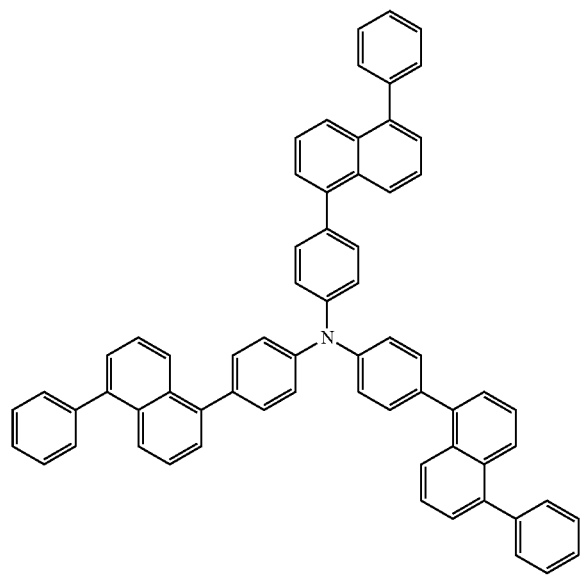

the structural formula (2)-9
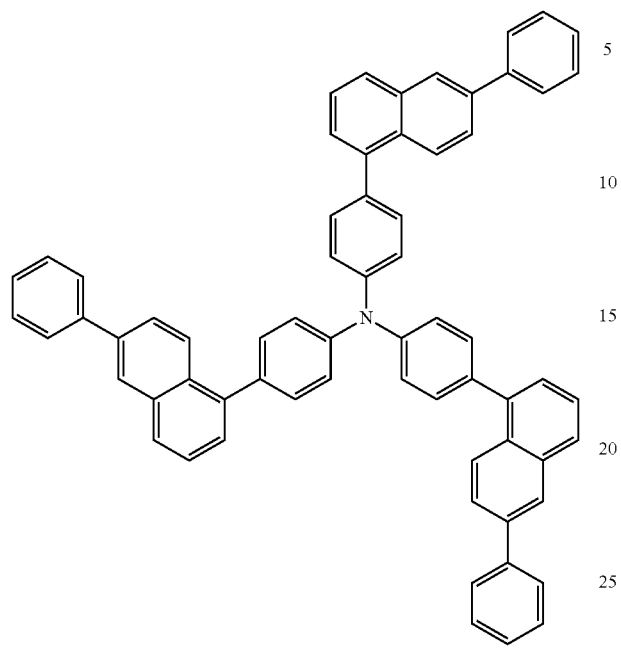
the structural formula (2)-11
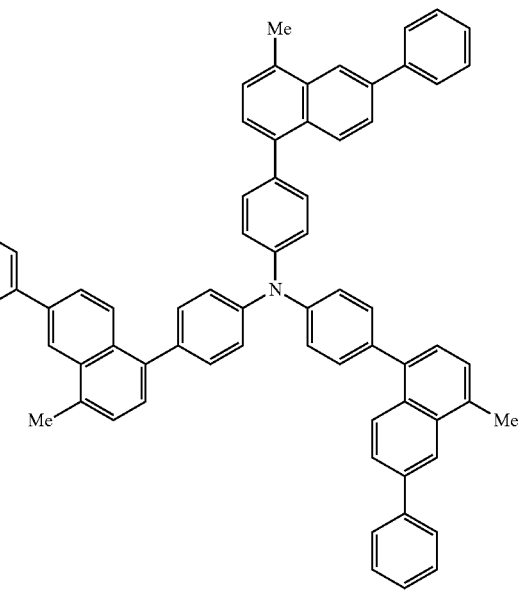
the structural formula (2)-10
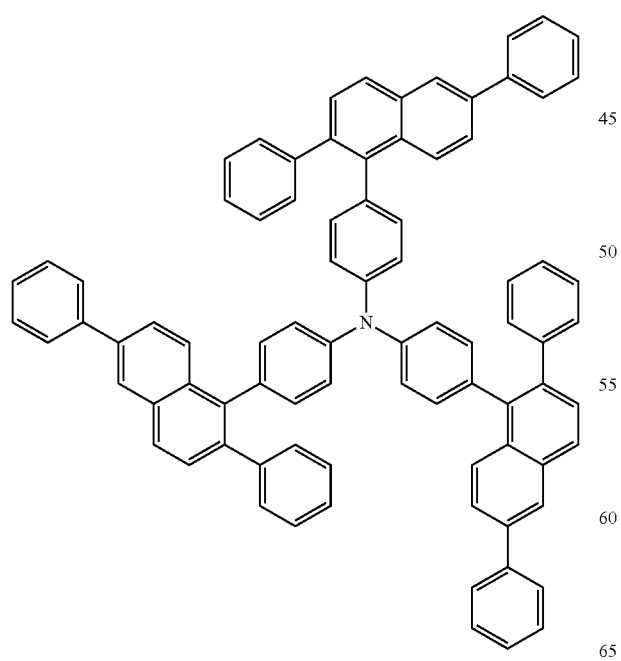
the structural formula (2)-12
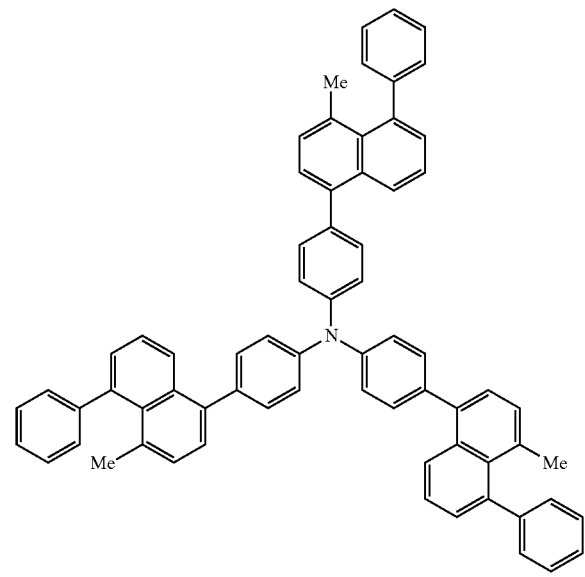

the structural formula (2)-13
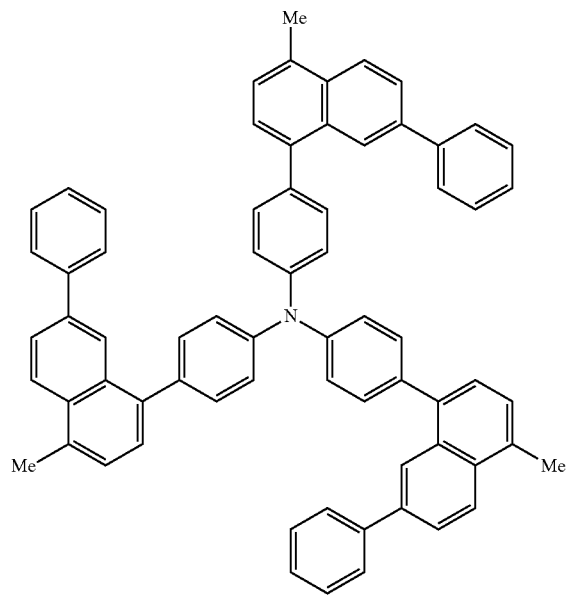
the structural formula (2)-14
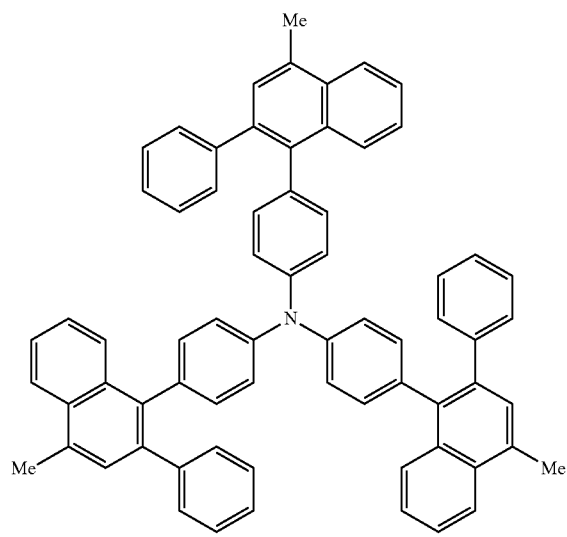
the structural formula (2)-15
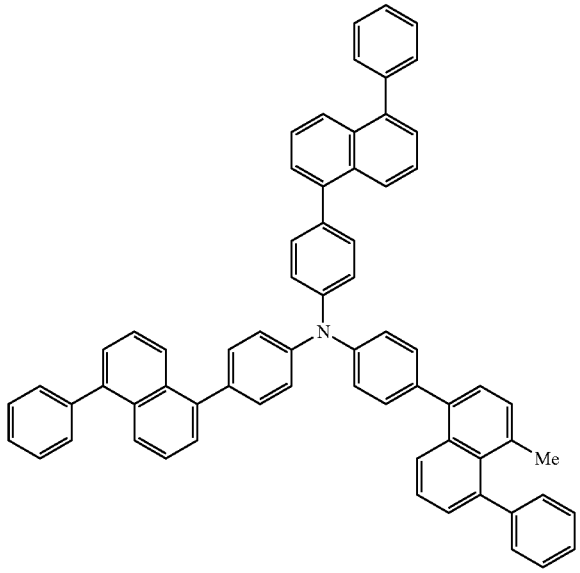
the structural formula (2)-16
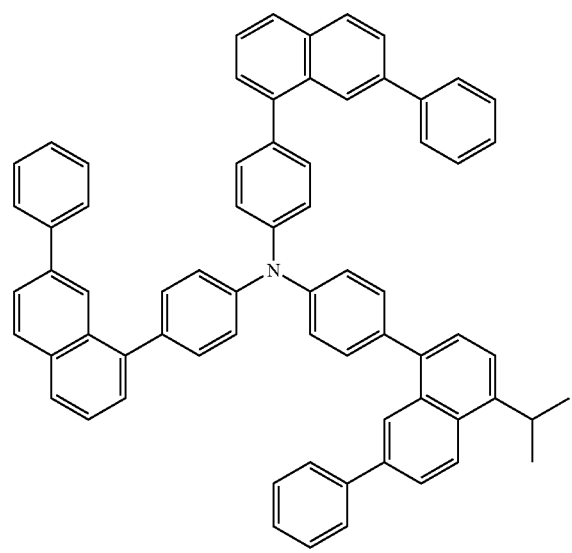
the structural formula (2)-17
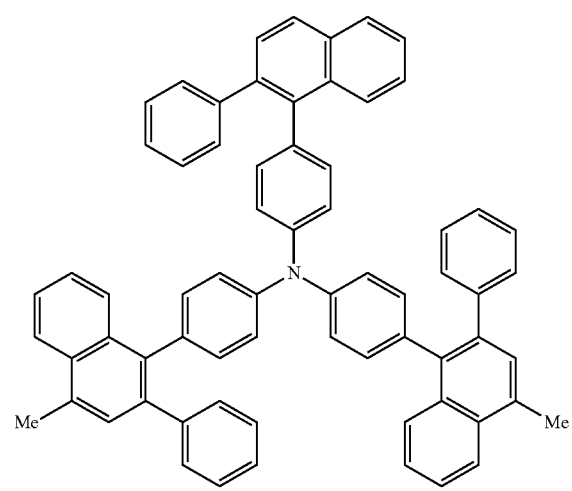

-continued
the structural formula (2)-18
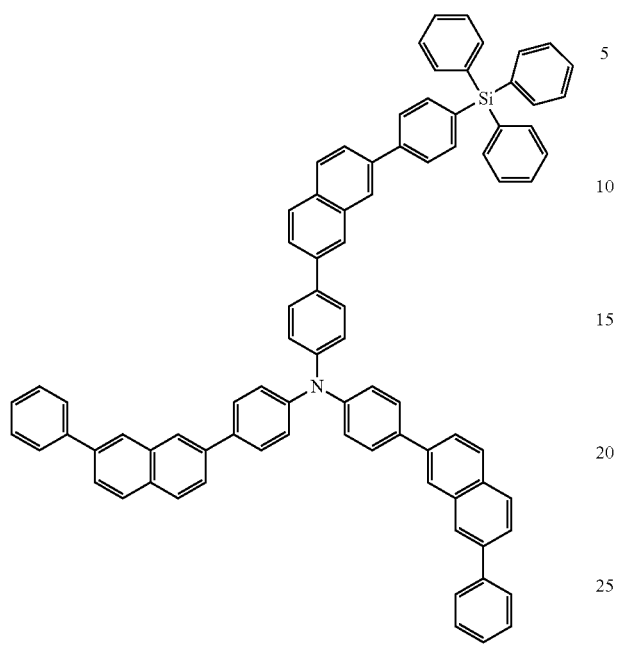
the structural formula (2)-20
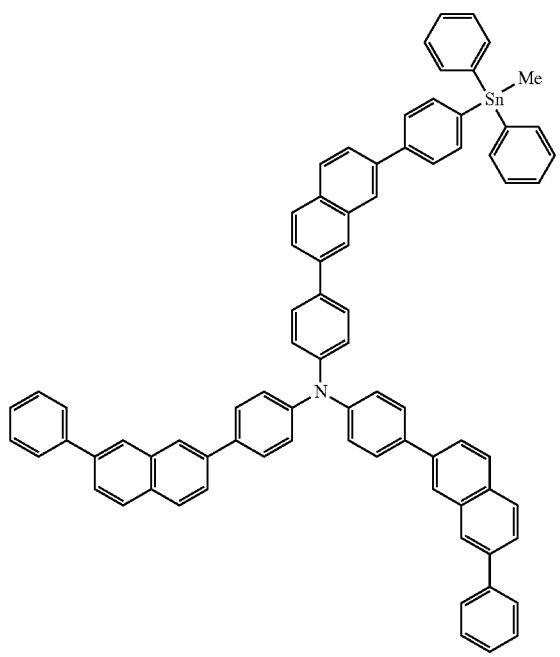
the structural formula (2)-19
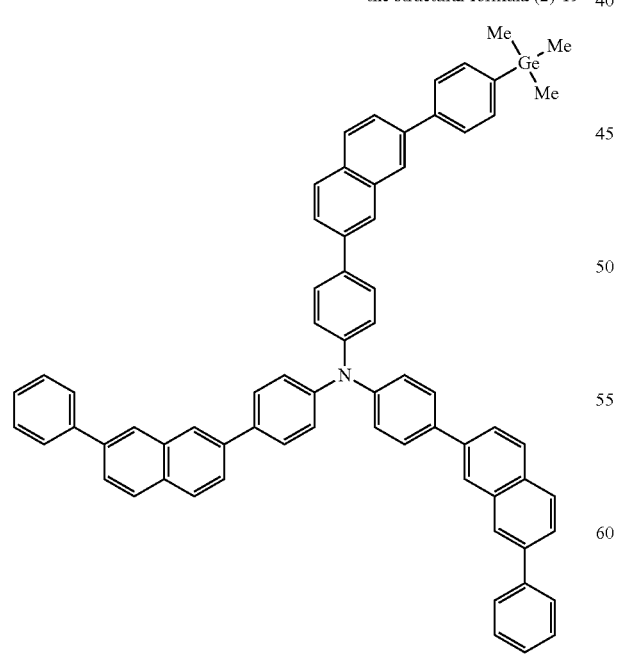
the structural formula (2)-21
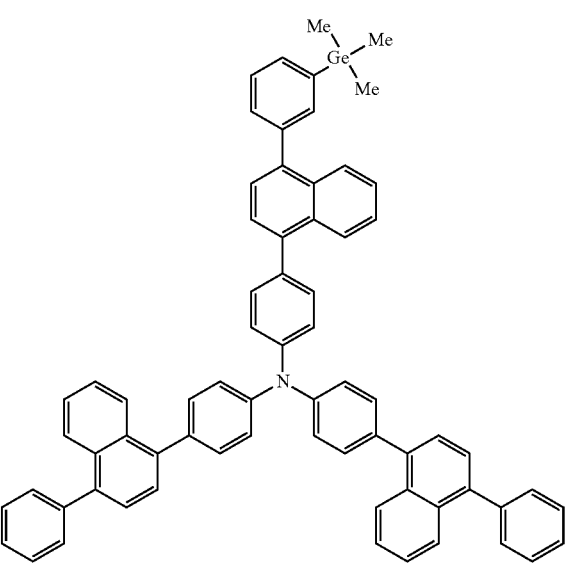

the structural formula (2)-22
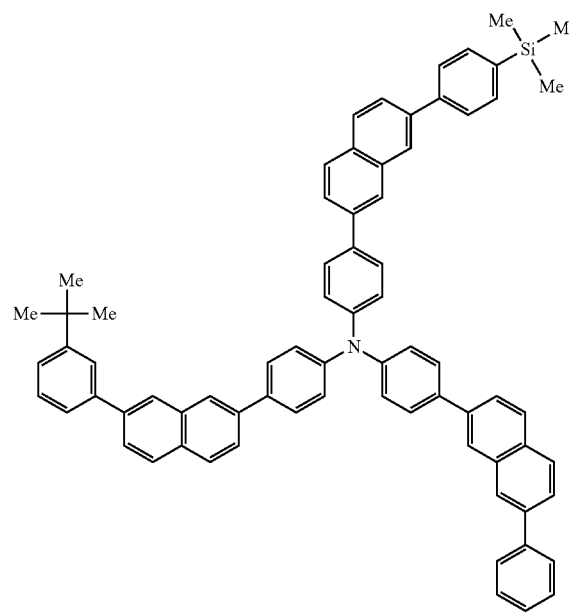
the structural formula (2)-24
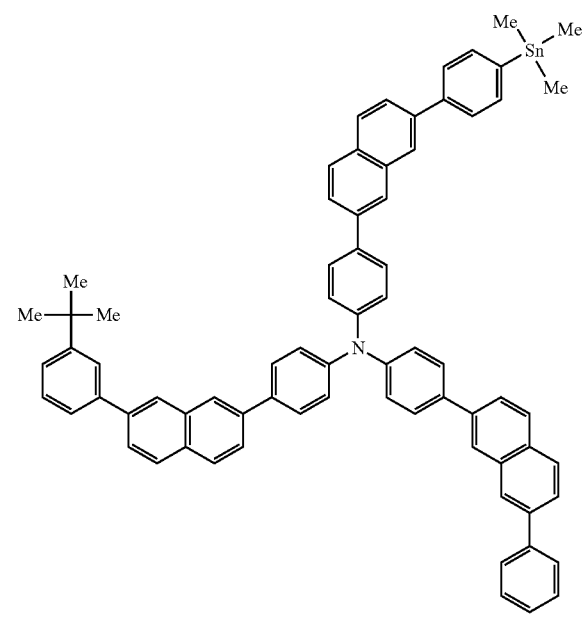
the structural formula (2)-23
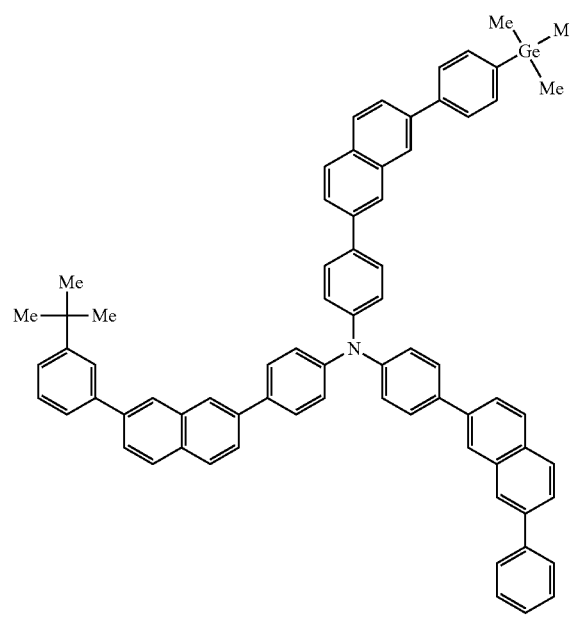
the structural formula (2)-25
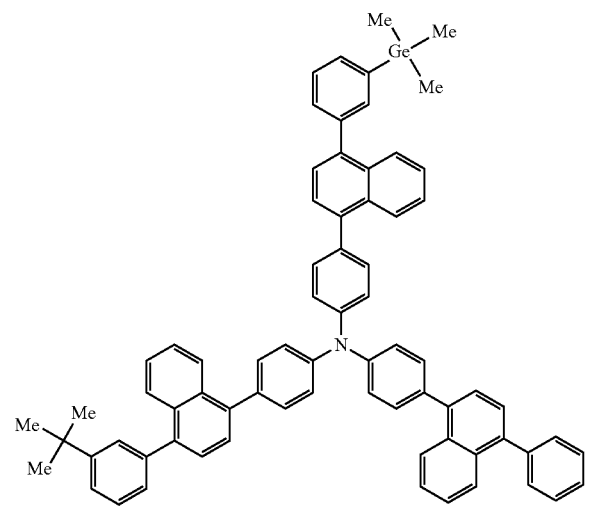

the structural formula (2)-26
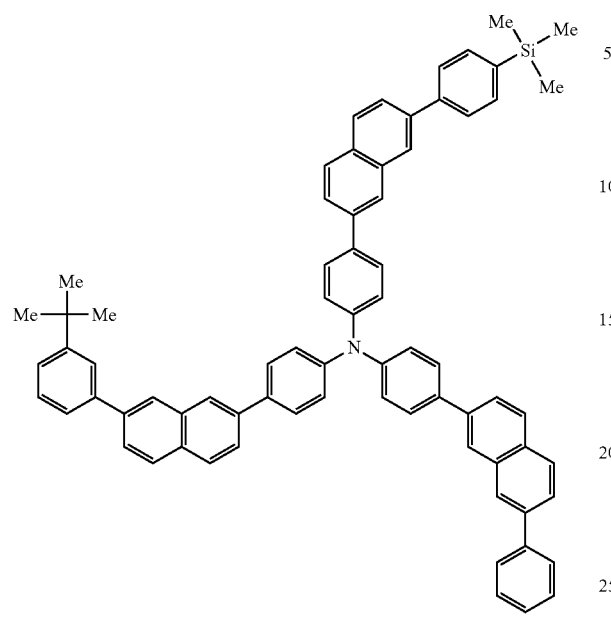
the structural formula (2)-28
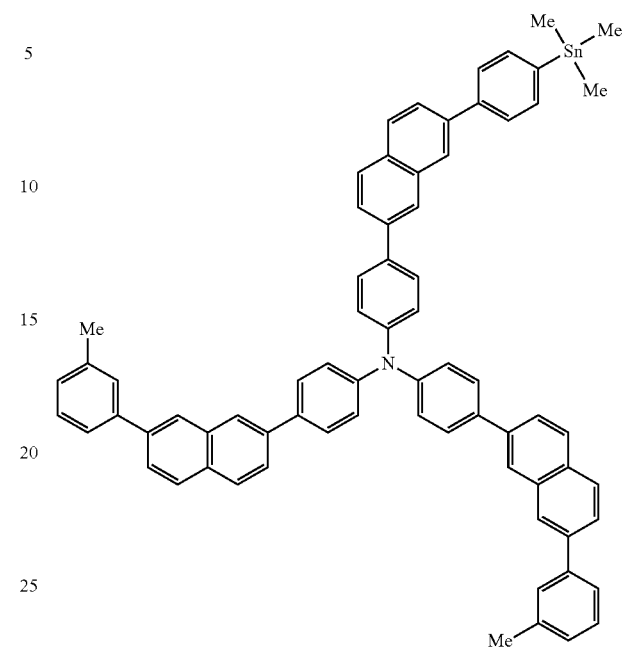
the structural formula (2)-27
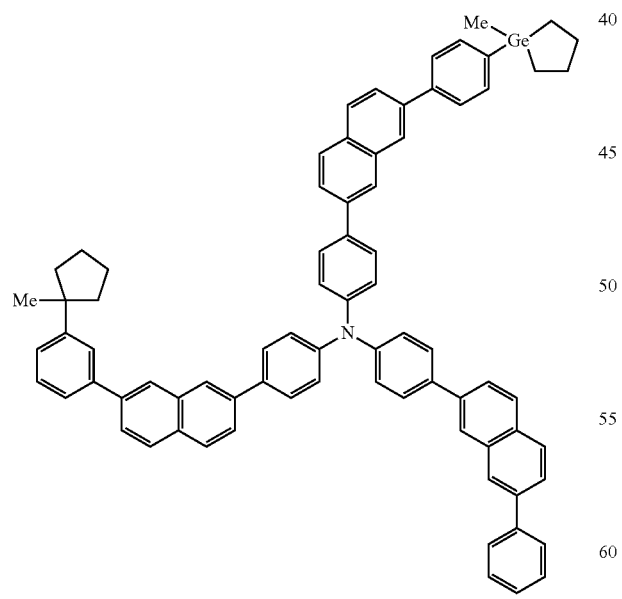
the structural formula (2)-29
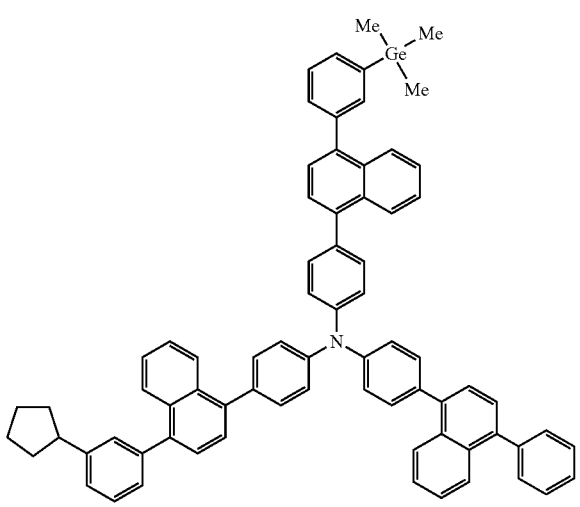

the structural formula (2)-30
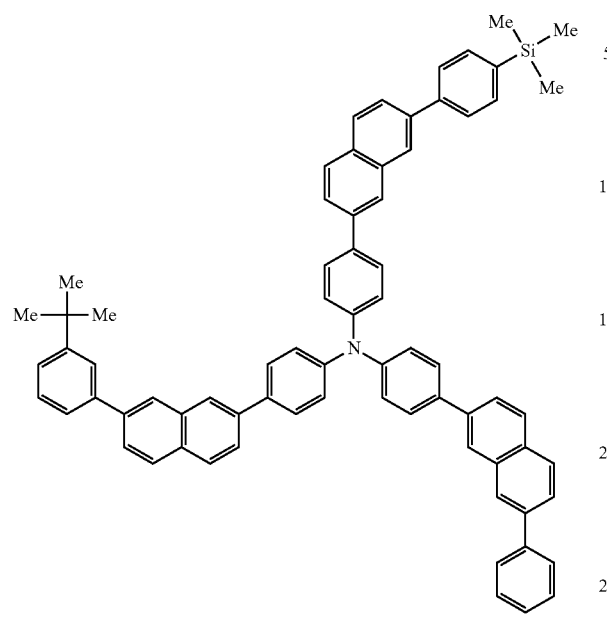
the structural formula (2)-32
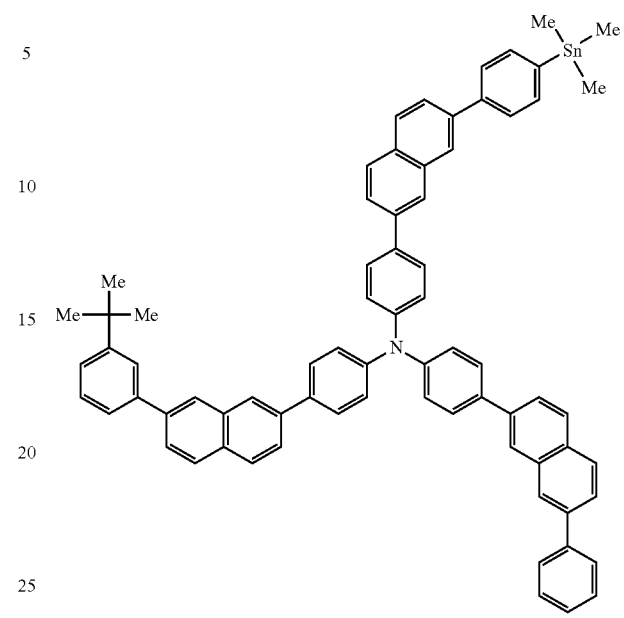
the structural formula (2)-31
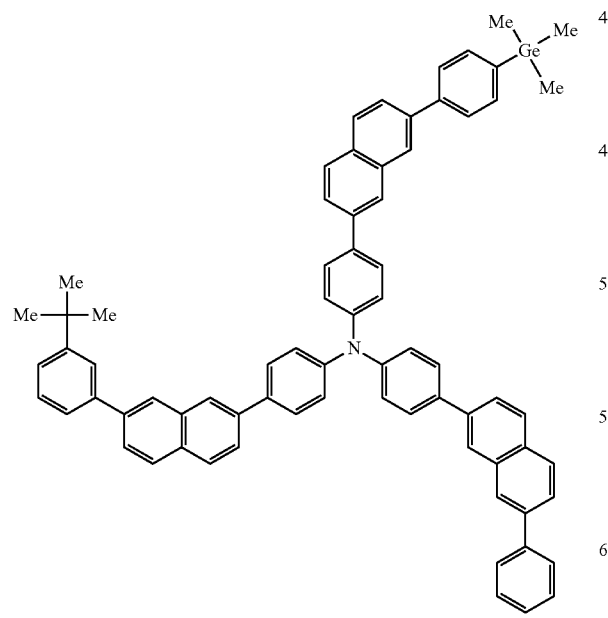
the structural formula (2)-33
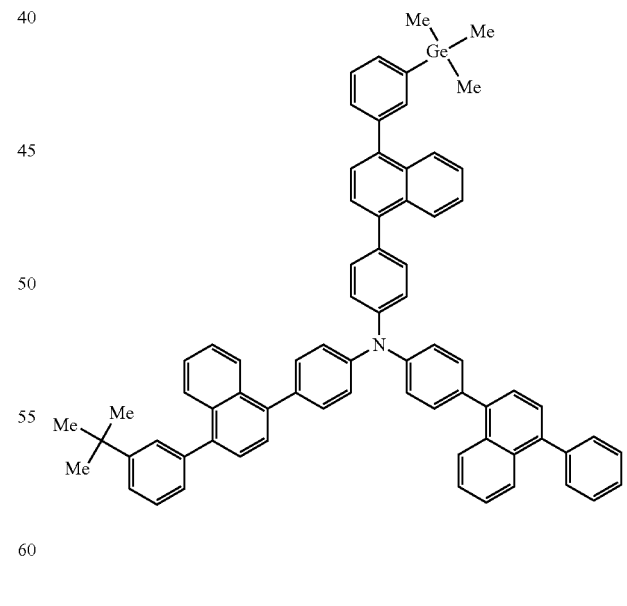

the structural formula (2)-34 the structural formula (2)-35 the structural formula (2)-36 the structural formula (2)-37

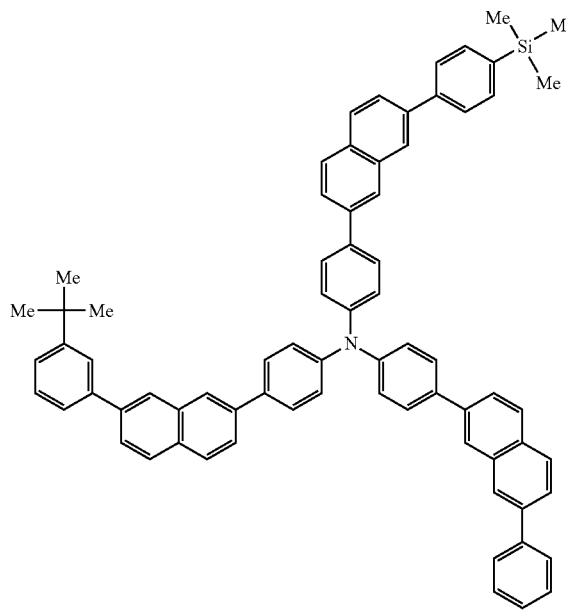
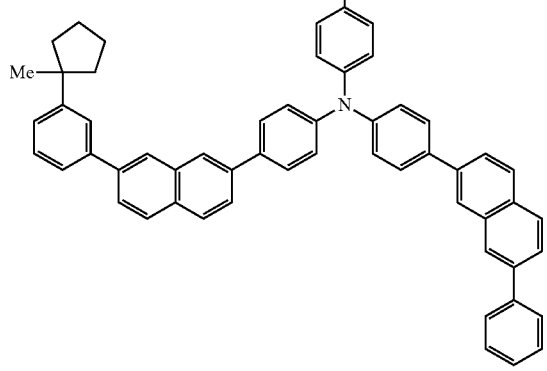

Firstly, the compounds represented by the structural formulas (2)-1 to (2)-17 are examples in which $R^1$ to $R^{33}$ in the general formula (2) are made the substituent groups which are selected from the alkyl group having the carbon number of 6 or less, the phenyl group, the naphthyl group, the phenanthrenyl group, and the anthrancenyl group.

As described above, when $R^9$, $R^{20}$ or $R^{31}$ in the general formula (2) is β-hydrogen, $R^4$, $R^{15}$ or $R^{26}$ in the naphthalene skeleton is either hydrogen or the alkyl group having the carbon number of 6 or less.

Next, the compounds represented by the structural formulas (2)-18 to (2)-37, respectively, are examples in which any one of $R^1$ to $R^{33}$ in the general formula (2) is made the substituent group which is selected from the phenyl group, the naphthyl group, the phenanthrenyl group, and the anthracenyl group, and for which the organic compound group of the 14-th group elements each heavier than carbon is substituted.

As described above, in the organic compound group in the general formula (2), the substituent group which is selected from the alkyl group having the carbon number of 6 or less, and the phenyl group, the naphthyl group, the phenanthrenyl group, and the anthracenyl group for each of which the alkyl group having the carbon number of 6 or less may be substituted may be bonded to the 14-th group element heavier than carbon. In addition, the groups bonded to the 14-th group element heavier than carbon may be linked to one another. For example, as shown in the structural formula (1)-30 or the like, the carbon elements bonded to the silicon (Si) element as the 14-th group element heavier than carbon may be linked to one another to form a ring. In addition, when $R^9$, $R^{20}$ or $R^{31}$ is β-hydrogen, and the 14-th group element is silicon (Si), $R^4$, $R^{15}$ or $R^{26}$ on the naphthalene skeleton is either hydrogen or the alkyl group having the carbon number of 6 or less.

It was confirmed that as shown in the following embodiment and Examples, the organic electroluminescence element having such a structure sustains the high luminous efficiency for a long time even under the high temperature condition.

Therefore, according to the present embodiments, the enhancement of the luminous efficiency of the organic electroluminescence element, and the long life promotion can be realized even under the high temperature condition. In addition, it is possible to realize the enhancement of the heat resistance property and the enhancement of the display characteristics in the display device using the organic electroluminescence element.

BRIEF DESCRIPTION OF THE DRAWINGS

FIG. 3 is a circuit diagram, partly in block, showing a circuit configuration of a display device according to another embodiment of the present invention;

FIGS. 9A to 9G are respectively a front view of mobile terminal equipment, for example, a mobile phone as a further example of application, in an open state, to which the another embodiment of the present invention is applied, a side elevational view thereof in the open state, a front view thereof in a close state, a left side elevational view thereof in the close state, a right side elevational view thereof in the close state, a top plan view thereof, and a bottom view thereof in the close state.

DETAILED DESCRIPTION OF THE PREFERRED EMBODIMENTS

The preferred embodiments of the present invention will be described in detail hereinafter with reference to the accompanying drawings. It is noted that the description will be given below in accordance with the following order.

Figure 1:
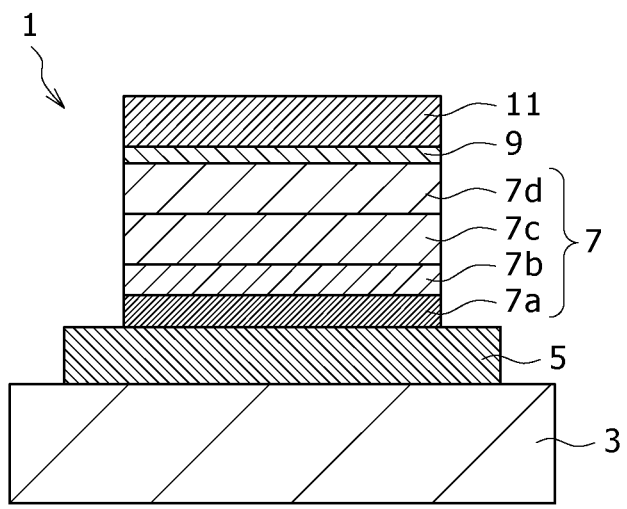
FIG. 1 is a cross sectional view showing a structure of an organic electroluminescence element according to an embodiment of the present invention.

1. Structure of Organic Electroluminescence Element
2. Configuration of Display Device
3. Application Examples
4. Examples and Comparative Examples 1. Structure of Organic Electroluminescence Element FIG. 1 is a cross sectional view schematically showing a structure of an organic electroluminescence element according to an embodiment of the present invention. The organic electroluminescence element 1 shown in FIG. 1 is structured in such a way that an anode 5 and an organic light emitting functional layer 7 are laminated in this order on a substrate 3, and a cathode 11 is laminated on the organic light emitting functional layer 7 through a cathode interface layer 9. Of these constituent elements 3, 5, 7, 9, and 11, the organic light emitting functional layer 7 is structured in the form of such a multilayer structure that, for example, a hole-injecting layer 7a, a hole transport layer 7b, a light emitting layer 7c, and an electron transport layer 7d are laminated in this order.

In particular, the feature of the organic electroluminescence element 1 according to the embodiment of the present invention is that at least one of the materials represented by the general formula (1) and general formula (2) described above, respectively, is contained in the multilayer structure composing the organic light emitting functional layer 7. Although these materials represented by the general formula (1) and general formula (2) described above, respectively, may be used in any of the hole-injecting layer 7a, the hole transport layer 7b, the light emitting layer 7c, and the electron transport layer 7d in the multilayer structure composing the organic light emitting functional layer 7, these materials are, preferably contained in the layer on the anode 5 side with respect to the light emitting layer 7c, and are more preferably contained in the layer which directly contacts an interface of the light emitting layer 7c on the anode 5 side. For this reason, in the embodiment, a structure in which at least one of the materials represented by the general formula (1) and general formula (2) described above, respectively, is contained in the hole transport layer 7b will be described below.

The following description will be given on the assumption that the organic electroluminescence element 1 having such a lamination structure is structured in the form of a top emission type element in which a light is taken out from the side of the cathode 11 made of a metallic material opposite to a side of the substrate 3. Thus, the details of the individual layers in this case will now be described so as to start from the substrate 3 side.

<Substrate>

The substrate 3 is a supporting body having one principal surface side on which the organic electroluminescence elements 1 are formed and arranged. For example, a quartz, a glass, a metallic foil, a film or sheet made of a resin, or the like is used as a material of the substrate 3. Of them, a quartz or a glass is preferably used as the material of the substrate 3. In the case where the substrate 3 is made of the resin, a polyester class such as a methacryl resin class typified by polymethylmethacrylate (PMMA), polyethylene terephthalate (PET), polyethylene naphthalate (PEN), or polybuthylene naphthalate (PBN), a polycarbonate resin or the like is given as the material of the substrate 3. In this case, however, it is necessary to adopt a lamination structure and a surface treatment for suppressing a water permeability and a gas permeability. In addition, in the case of the top emission structure in which a light is taken out from a top portion, the substrate itself needs not to have an optical transparency, and thus, for example, a Si substrate may be used. In the case of an active element, the active element can be directly formed on the Si substrate to be used.

<Anode>

A material which has a large work function from a vacuum level of an electrode material for the purpose of efficiently injecting holes is used as the anode 5. For example, a metal such as aluminum (Al), chromium (Cr), molybdenum (Mo), tungsten (W), copper (Cu), silver (Ag), or gold (Au), and an alloy thereof, and also an oxide of such a metal or alloy, or an alloy of a tin oxide ($SnO_2$) and antimony (Sb), an alloy of an indium tin oxide (ITO), an indium zinc oxide (InZnO) or a zinc oxide (ZnO), and aluminum (Al), an oxide of such a metal and an alloy, or the like is used either singularly or in a mixed state.

In addition, the anode 5 may have a lamination structure composed of a first layer which is excellent in light reflection property, and a second layer which is provided on an upper portion of the first layer, and which has the optical transparency and a large work function.

Here, preferably, an alloy mainly containing aluminum as a principal component is used in the first layer. An accessary component of the alloy contains therein at least one element which is relatively smaller in work function than aluminum as the principal component. A lanthanoid series element is preferable as such an accessary component. Although the work function of the lanthanoid series element is not large, the lanthanoid series element contains therein these elements, whereby the stability of the anode is enhanced and the hole injection property of the anode 5 is also met. In addition, the first layer may contain therein an element such as silicon (Si) or copper (Cu) as the accessary component in addition to the lanthanoid series element.

A content of the accessary component in the aluminum alloy layer composing the first layer, for example, is preferably equal to or smaller than 10 wt % in total in the case of Nd, Ni, Ti or the like for stabilizing aluminum. As a result, the aluminum alloy layer can be stably held in the process for manufacturing the organic electroluminescence element while a reflectivity in the aluminum alloy layer is maintained, and moreover the processing precision and the chemical stability can be obtained. In addition, it is also possible to improve the conductive property of the anode 5, and the adhesion between the substrate 3 and the anode 5.

In addition, a layer made of at least one of an oxide of an aluminum alloy, an oxide of molybdenum, an oxide of zirconium, an oxide of chromium, and an oxide of tantalum can be exemplified as the second layer. Here, for example, when the second layer is an oxide layer (including a natural oxide film) of an aluminum alloy containing therein a lanthanoid series element as the accessary component, a transmittance of the second layer containing therein the oxide of the lanthanoid series element becomes satisfactory because the transmittance of the oxide of the lanthanoid series element is large. For this reason, the high reflectivity can be maintained in the surface of the first layer. In addition, the second layer may also be a transparent conductive layer made of an Indium Tin Oxide (ITO), an Indium Zinc Oxide (IZO) or the like. The electron injection characteristics of the anode 5 can be improved by using such a conductive later.

In addition, the anode 5 may be provided with a conductive layer for enhancing the adhesion between the anode 5 and the substrate 3 on the side contacting the substrate 11. A transparent conductive layer made of the ITO, the IZO or the like is given as such a conductive layer.

Also, when a driving system for the display device configured by using the organic electroluminescence element 1 is an active matrix system, the anode 5 is patterned every pixel, and is provided in a state of being connected to corresponding one of thin film transistors for driving provided on the substrate 3. In this case, it is supposed that an insulating film (not shown) is provided so as to overlie each of the anodes 5, and surfaces of the anodes 5 of the pixels are exposed through opening portions of the insulating film, respectively.

<Hole Injecting Layer>

The hole injecting layer 7a is provided for enhancing the efficiency of injecting holes from the anode 5 to the light emitting layer 7c. Benzidine, styrylamine, triphenylamine, porphyrin, triphenylene, azatriphenylene, tetracyanoquinodimethane, triazole, imidazole, oxadiazole, polyarylalkane, phenylenediamine, arylamine, oxazole, anthracene, fluorenone, hydrazone, stilbene or a derivative thereof, or a heterocyclic conjugated system monomer such as a polysilane system compound, a vinylcarbazole system compound, a thiophene system compound, or aniline, oligomer or polymer, for example, can be used as a material composing such a hole injecting layer 7a.

In addition, although α-naphthylphenylenediamine, porphyrin, metal tetraphenylporphyrin, metal naphthalocyanine, hexacyanoazatriphenylene, 7, 7, 8, 8-tetracyanoquinodimethane (TCNQ-TCNQ), 7, 7, 8, 8-tetracyano-2, 3, 5, 6-tetrafluoroquinodimethane (F4-TCNQ), 4, 4, 4-tris(3-methylphenylphenylamino)triphenylamine, N, N, N', N'-tetrakis (p-tolyl)p-phenylenediamine, N, N, N', N'-tetraphenyl-4, 4'-diaminobiphenyl, N-phenylcarbazole, 4, 4'-bis(p-tolylamino)stilbene, poly(paraphenylenevinylene), poly (thiophenevinylene), poly(2, 2'-thienylpyrrole), or the like is given as a more concrete material of the hole injecting layer 7a, the present embodiment is by no means limited thereto. In addition, the hole injecting layer 7a made of such a material may also have a lamination structure.

<Hole Transport Layer>

The hole transport layer 7b is provided for enhancing the efficiency of injecting the holes from the anode 5 side to the light emitting layer 7c. In particular, the feature of the embodiment of the present invention is that the hole transport layer 7b is made of at least one of the materials represented by the general formulas (1) and (2) described above, respectively. In addition, the hole transport layer 7b made of the material as described above may have the lamination structure.

<Light Emitting Layer>

The light emitting layer 7c is a region in which when a suitable voltage is applied across the anode 5 and the cathode 11, the holes injected from the anode 5 side, and the electrons injected from the cathode 11 side are recombined with each other. In the embodiment, an arbitrary luminescence material can be selected from the known luminescence materials in related art in order to be used. For example, a polycondensed aromatic compound, fluorescent whiting agent such as a benzoxazole system, a benzothiazole system, or a benzimidazole system, or a compound, having an excellent thin film forming property, such as a metal chelated oxanoid compound or a distyrylbenzene system compound can be used as such a luminescence material. Here, for example, anthracene, naphthalene, phenanthrene, pyrene, chrysene, a condensed-ring luminescence material containing a perylene skeleton, other condensed-ring luminescence materials each containing therein about 8 condensed rings, or the like can be given as the polycondensed aromatic compound described above. Specifically, 1, 1, 4, 4-tetraphenyl-1, 3-butadiene, 4, 4'-(2, 2-diphenylvinyl)biphenyl or the like can be used as the polycondensed aromatic compound described above. The light emitting layer either may be composed one layer made of one kind of luminescence material or two or more kinds of luminescence materials, or may be obtained by lamination of a light emitting layer made of a compound different from that composing the light emitting layer concerned.

In addition, the light emitting layer 7c may be provided in the form of a light emitting layer having a hole transport property, a light emitting layer having an electron transport property, or a light emitting layer having both hole and electron transport properties in the organic electroluminescence element 1.

Moreover, the light emitting layer 7c may be a layer containing therein a phosphorescence luminescence material and a host material. It is noted that when the light emitting layer 7c is made of the phosphorescence luminescence material, preferably, as exemplified in the above structural formulas (1)-22 to (1)-41, and the above structural formulas (2)-18 to (2)-37, the light emitting layer 7c is made of the material having the organic compound group of the 14-th group elements each heavier than carbon.

<Electron Transport Layer>

The electron transport layer 7d is provided for transporting the electrons injected from the cathode 11 to the light emitting layer 7c. For example, quinoline, pelylene, phenanthroline, styryl, pyrazine, triazole, oxazole, fullerene, oxadiazole, fluorenone, or a derivation or metal complex thereof is given as the material of the electron transport layer 7d. Specifically, tris(8-hydroxyquinoline)aluminum (abbreviated as Alq3), anthracene, naphthalene, phenanthrene, pyrene, anthracene, perylene, butadiene, coumalin, C60, acridine, stilbene, 1, 10-phenanthroline, or a derivation or metal complex thereof is given as the material of the electron transport layer 7d. Such an electron transport layer 7d may have a lamination structure.

It is noted that the organic light emitting functional layer 7 structured as the lamination structure as described above has to be provided with at least a light emitting layer 7c and the hole transport layer 7b contacting the light emitting layer 7c, and also any other necessary lamination structure can be selected for the organic light emitting functional layer 7.

<Cathode Transport Layer>

The cathode interface layer 9 is used as an electron injecting layer and is made of a material which has a small work function and an excellent optical transparency. For example, a lithium oxide ($Li_2O$) as an oxide of lithium, cesium carbonate ($Cs_2CO_3$) as a complex oxide of cesium (Cs), or a mixture of an oxide and an complex oxide thereof can be used as such a material. In addition, the material of the cathode interface layer 9 is by no means limited to such a material. That is to say, for example, an alkaline earth metal such as calcium (Ca) or barium (Ba), an alkaline metal such as lithium or cesium, a metal, having a small work function, such as indium (In) or magnesium (Mg), an oxide, a complex oxide and a fluoride thereof, or the like may also be used in the form, of, an elementary substance, or a mixture or alloy of an oxide, a complex oxide and a fluoride thereof with an increased stability.

<Cathode>

The cathode 11, for example, is made of a metallic material and has an optical transparency. In addition, when the organic electroluminescence element 1 is structured in the form of a resonance structure, the cathode 11 is structured so as to have a semi-transmissive semi-reflexible property. As a result, a light generated in the light emitting layer 7c can be effectively taken out with satisfactory color purity.

Such a cathode 11, for example, is formed from a thin film using a layer, such as a MgAg layer, having an optical transparency. This metallic cathode layer may be further a mixture layer containing therein an organic luminescence material such as an aluminum quinoline complex, a styrylamine derivative, or a phthalocyamine derivative. In this case, the cathode 11 may specially further have a layer, such as a MgAg layer, having an optical transparency as a third layer.

When the display device configured by using the organic electroluminescence element 1 utilizes the active matrix system, such a cathode 11 is formed on the substrate 3 so as to be insulated from the anode 5 through the organic light emitting functional layer 7 or the like, and is used as a common electrode of the pixels.

When the organic electroluminescence element 1 structured in the manner as described above has the resonance structure, an emitted light which is multiply interfered between a light reflective surface of the cathode 11 structured so as to have the semi-transmissive semi-reflexible property as described above, and a light reflective surface on the anode 5 side is taken out from the cathode 11 side. In this case, an optical distance between the light reflective surface on the anode 5 side and the light reflective surface on the cathode 11 side is regulated by a wavelength of a light which is desired to be taken out. Also, the thicknesses of the layers 7a to 7d, and 9 are set so as to meet the optical distance. Also, in such a top emission type organic electroluminescence element 1, this cavity structure is positively used, whereby the improvement in the efficiency of taking out the light to the outside, and the control for the emission spectrum can be carried out.

Here, the layers from the anode 5 to the cathode 11 described above can be formed by using a dry process such as a vacuum evaporation method, an ion beam method (EB method), a molecular beam epitaxy method (MBE method), a sputtering method, or an Organic Vapor Phase Deposition (OVPD) method.

In addition, in particular, when the organic light emitting functional layer 7 is made of the organic material, the layers from the anode 5 to the cathode 11 described above can also be formed by using a wet process such as a coating method such as a laser transfer method, a spin coat method, a dipping method, a doctor blade method, an ejection coat method, or a spray coat method, or a printing method such as an ink jet method, an offset printing method, a relief printing method, an intaglio printing method, a screen printing method, or a micro-gravure coat method in addition to the methods described above. Thus, the dry process and the wet process may also be used in combination with each other depending on the properties of the organic layers and the members.

In addition, when the layers from the anode 5 to the cathode 11 are formed through the patterning, for example, an evaporation method or transfer method using masks can be applied thereto.

It was confirmed that the organic electroluminescence element 1 according to the embodiment of the present invention which is structured in the manner as described above, as will be shown in Examples, sustains the high luminous efficiency for a long time even under the high temperature condition.

It is noted that the lamination structure from the anode 5 to the cathode 11 shown in the embodiment described above is merely an example, and thus the hole injecting layer 7a, the hole transport layer 7b, the electron transport layer 7d, and the cathode interface layer 9 other than the anode 5, the cathode 11 and the light emitting layer 7c may be omitted as may be necessary, or a new functional layer(s) can be added to the lamination structure.

Figure 2:
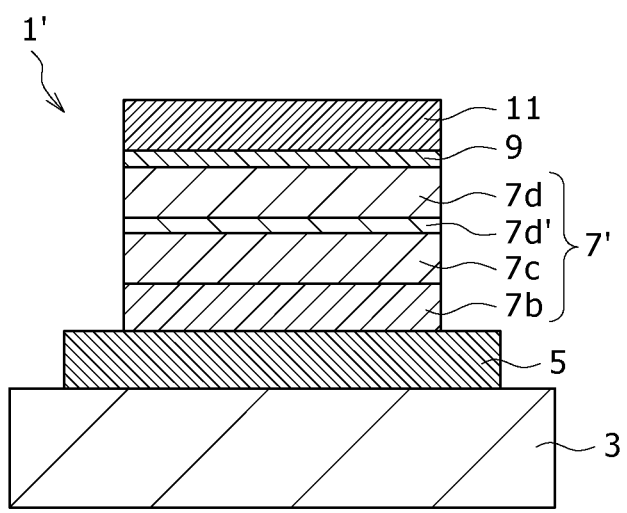
FIG. 2 is a cross sectional view showing a structure of an organic electroluminescence element according to a change of the embodiment of the present invention.

For example, like an organic electroluminescence element 1' shown in FIG. 2, the hole injecting layer 7a may be omitted in the organic light emitting functional layer 7', and moreover a hole blocking layer 7d' may be provided between the light emitting layer 7c and the electron transport layer 7d. The hole blocking layer 7d' is a layer for blocking a movement of the holes from the light emitting layer 7c to the cathode 11 side. By providing the hole blocking layer 7d', the hole density within the light emitting layer 7c is prevented from being reduced.

Since an organic electroluminescence element 1' is preferably, especially applied to the structure in which the light emitting layer 7c containing therein the phosphorescence luminescence material is provided.

Here, in the organic electroluminescence element 1, 1' including the light emitting layer 7c having the phosphorescence luminescence property, a triplet energy (excited energy) diffused from the light emitting layer 7c to the hole transport layer 7d side contributes to the deterioration of the element in some cases. This, for example, is described in "IEEE PHOTO. TECHN. LETT. 20," (16), 2008. However, since the dissipation of the excited energy diffused to the hole transport layer 7b to the external system was not enough, the excited energy was accumulated in the element, and thus it was difficult to lengthen the element life. Then, it was found out that the 14-th group element heavier than carbon is contained in the hole transport layer 7b, thereby obtaining the phosphorescence element having a combination of the high heat resistance property and the long life as will be shown in Examples.

In addition, in the embodiment described above, the present invention has been described in detail by exemplifying the case where the organic electroluminescence element is of the top emission type. However, the organic electroluminescence element of the present invention is by no means limited to the application to the top emission type, and thus can be widely applied to the structure in which the organic light emitting functional layer 7 having at least the light emitting layer 7c is held between the anode 5 and the cathode 11. Therefore, the organic electroluminescence element of the present invention can also be applied to a structure in which the cathode 11, the cathode interface layer 9, the organic light emitting functional layer 7, and the anode 5 are laminated in order so as to start from the substrate 3 side, or a bottom emission type (so-called transmission type) organic electroluminescence element designed in such a way that an electrode located on the substrate 3 side (a lower electrode either as a cathode or as an anode) is made of a transparent material, and an electrode located on a side opposite to the substrate 3 (an upper electrode either as the cathode or as the anode) is made of a reflective material, thereby taking out a light only from the lower electrode side.

2. Configuration of Display Device

FIG. 3 is a circuit diagram, partly in block, showing a circuit configuration of a display device configured by using the organic electroluminescence element 1 of the embodiment described above. In this case, a display device 21 utilizing an active matrix system and using the organic electroluminescence element 1 will be described below.

As shown in FIG. 3, a display area 3a and a circumference area 3b thereof are set on the substrate 3 of the display device 21. A plurality of scanning lines 23 and a plurality of signal lines 24 are wired on the display area 3a transversely and longitudinally, respectively, and pixels are provided so as to correspond to intersection points between a plurality of scanning lines 23 and a plurality of signal lines 24, thereby configuring a pixel array. In addition, a scanning line drive circuit 25 for scanning and driving the scanning lines 23, and a signal line drive circuit 26 for supplying a video signal (that is, an input signal) corresponding to luminous information to the signal lines 24 are disposed in the circumference area 3b.

Each of pixel circuits provided in the respective intersection points between the scanning lines 23 and the signal lines 24, for example, is composed of a thin film transistor Tr1 for switching, a thin film transistor Tr2 for driving, a hold capacitor Cs, and the organic electroluminescence element 1 described with reference to FIG. 1. Also, the video signal which has been written from the corresponding one of the signal lines 24 through the thin film transistor Tr1 for switching is held in the hold capacitor Cs by driving of the scanning line drive circuit 25. In addition, a current corresponding to an amount of signal thus held is supplied from the thin film transistor Tr2 for driving to the anode 5 of the organic electroluminescence element 1, so that the organic electroluminescence element 1 emits a light at a luminance corresponding to this current value. It is noted that the thin film transistor Tr2 for driving, and the hold capacitor Cs are each connected to a power source supply line (Vcc) 27 common thereto. In addition, the cathode 11 of the organic electroluminescence element 1 is provided as an electrode common to all the pixels, and is connected to the ground potential GND.

It is noted that the configuration of the pixel circuit as described above is merely an example, and thus a capacitor element(s) may be provided within the pixel circuit as may be necessary, and a plurality of transistors may be provided in the pixel circuit, thereby configuring the pixel circuit. In addition, a necessary drive circuit is added to the circumference area 3b as may be necessary in accordance with a change in configuration of pixel circuit.

Figure 4:
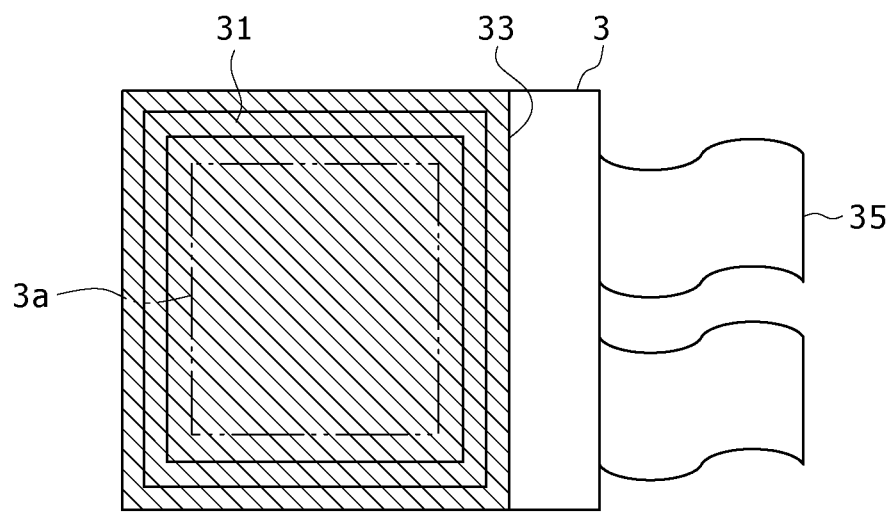
FIG. 4 is a structural view showing a module-shaped display device, having a sealed structure, to which the another embodiment of the present invention is applied.

In addition, the display device 21 according to another embodiment of the present invention described above also includes one having a module shape having a sealed structure as shown in FIG. 4. For example, a display module which has a sealing portion 31 provided so as to surround the display area 3a as the pixel array portion, and which is stuck to a facing portion (a sealing substrate 33) such as a transparent glass with the sealing portion 31 as an adhesive agent to be formed corresponds to the display device having the module shape as shown in FIG. 4. The transparent sealing substrate 33 may also be provided with a color filter, a protective film, a light blocking film and the like. It is noted that the substrate 3, as the display module, having the display area 3a formed therein may be provided with a flexible printed wiring board 35 through which a signal or the like is input/output to/from the display area 3a (pixel array portion) from/to the outside.

Since the display device 21 having the configuration described above is composed of the organic electroluminescence element 21 which sustains the high luminous efficiency for a long time even under the high temperature condition, the enhancement of the heat resistance property, and the improvement in the display characteristics are realized for the display device 21 having the circuit configuration described above.

It is noted that the embodiment has been described, as the another embodiment described above, in which the present invention is applied to the active matrix type display device. However, the display device of the present invention can also be applied to a passive matrix type display device. In this case, the same effects as those in the another embodiment can be obtained. In addition, in this case, for example, the organic electroluminescence element 1' described above with reference to FIG. 2 may be used instead of using the organic electroluminescence element 1 described above with reference to FIG. 1.

3. Application Examples

The display device 21 according to the another embodiment of the present invention described above is provided as a display portion in each of various kinds of electronic apparatuses which will be shown in FIG. 5 to FIGS. 9A to 9G. For example, the display device 21 according to the another embodiment of the present invention described above can be applied to the display devices, of electronic apparatuses in all the fields, in each of which a video signal input to the electronic apparatus, or a video signal generated in the electronic apparatus is displayed in the form of an image or a video image. These electronic apparatuses are typified by various electric apparatuses, shown in FIG. 5 to FIGS. 9A to 9G, such as a digital camera, a notebook-size personal computer, mobile terminal equipment such as a mobile phone, and a video camera. Hereinafter, examples of electronic apparatuses to each of which the display device 21 according to the another embodiment of the present invention is applied will be described.

Figure 5:
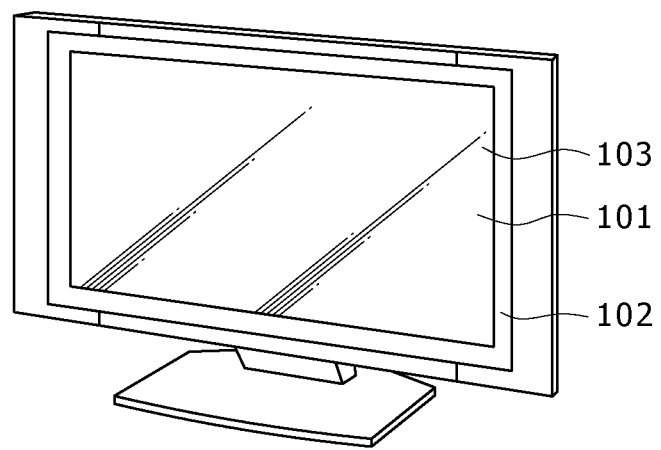
FIG. 5 is a perspective view of a television set as an example of application to which the another embodiment of the present invention is applied.

FIG. 5 is a perspective view showing a television set, as an example of application, to which the another embodiment of the present invention is applied. The television set according to the example of application includes an image display screen portion 101 composed of a front panel 102, a filter glass 103, and the like. Also, the television set is manufactured by using the display device 21 according to the another embodiment of the present invention as the image display screen portion 101.

Figure 6A:
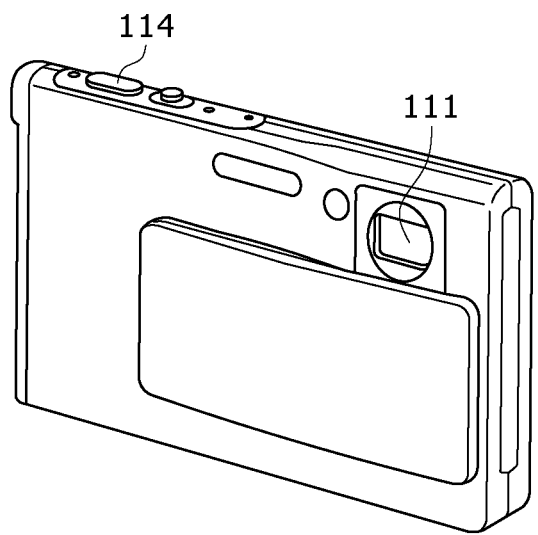
FIGS. 6A and 6B are respectively a perspective view of a digital camera as another example of application, when viewed from a front side, to which the another embodiment of the present invention is applied, and a perspective view of the digital camera as the another example of application, when viewed from a back side, to which the another embodiment of the present invention is applied.
Figure 6B:
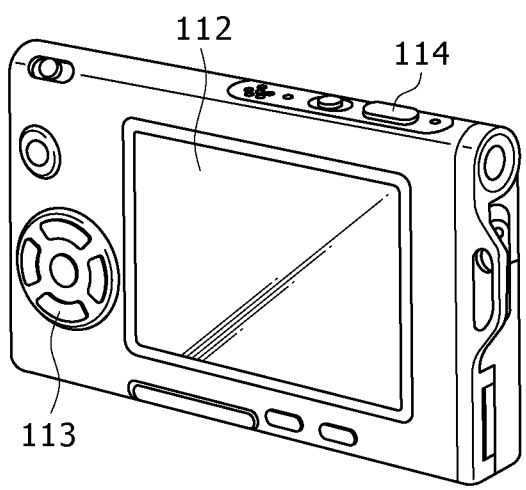

FIGS. 6A and 6B are respectively perspective views each showing a digital camera, as another example of application, to which the another embodiment of the present invention is applied. FIG. 6A is a perspective view when the digital camera is viewed from a front side, and FIG. 6B is a perspective view when the digital camera is viewed from a back side. The digital camera according to the another example of application includes a light emitting portion 111 for flash, a display portion 112, a menu switch 113, a shutter button 114, and the like. The digital camera is manufactured by using the display device 21 according to the another embodiment of the present invention as the display portion 112.

Figure 7:
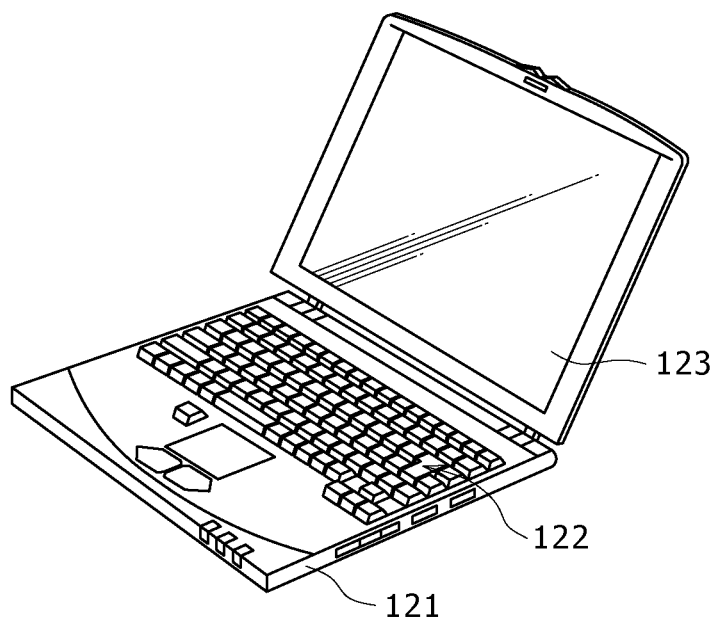
FIG. 7 is a perspective view showing a notebook-size personal computer as still another example of application to which the another embodiment of the present invention is applied.

FIG. 7 is a perspective view showing a notebook-size personal computer, as still another example of application, to which the another embodiment, of the present invention is applied. The notebook-size personal computer according to the still another example of application includes a main body 121, a keyboard 122 which is manipulated when characters or the like are input, a display portion 123 for displaying thereon an image, and the like. The notebook-size personal computer is manufactured by using the display device 21 according to the another embodiment of the present invention as the display portion 123.

Figure 8:
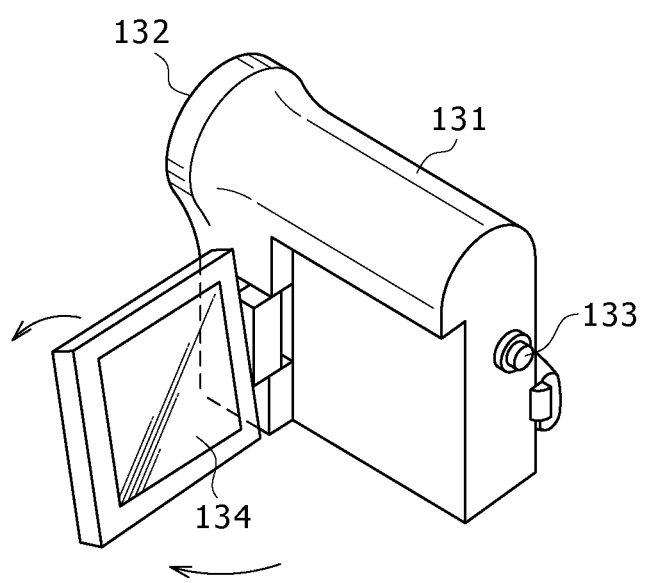
FIG. 8 is a perspective view showing a video camera, as yet another example of application, to which the another embodiment of the present invention is applied.

FIG. 8 is a perspective view showing a video camera, as yet another example of application, to which the another embodiment of the present invention is applied. The video camera according to the yet another example of application includes a main body portion 131, a lens 132 which captures an image of a subject and which is provided on a side surface directed forward, a start/stop switch 133 which is manufactured when an image of a subject is captured, a display portion 134, and the like. The video camera is manufactured by using the display device 21 according to the another embodiment of the present invention as the display portion 134.

FIGS. 9A to 9G are respectively views showing mobile terminal equipment, for example, a mobile phone, as a further example of application, to which the another embodiment of the present invention is applied. FIG. 9A is a front view in an open state of the mobile phone, FIG. 9B is a side elevational view in the open state of the mobile phone, FIG. 9C is a front view in a close state of the mobile phone, FIG. 9D is a left side elevational view in the close state of the mobile phone, FIG. 9E is a right side elevational view in the close state of the mobile phone, FIG. 9F is a top plan view in the close state of the mobile phone, and FIG. 9G is a bottom view in the close state of the mobile phone. The mobile phone according to the further example of application includes an upper chassis 141, a lower chassis 142, a connection portion (a hinge portion in this case) 143, a display portion 144, a sub-display portion 145, a picture light 146, a camera 147, and the like. The mobile phone is manufactured by using the display device 21 according to the another embodiment of the present invention either as the display portion 144 or as the sub-display portion 145.

4. Examples and Comparative Examples

Examples 1 and 2, and Comparative Examples 1 to 3

The organic electroluminescence element 1 having the structure described with reference to FIG. 1 was manufactured in the manner which will be described below.

Firstly, an ITO transparent electrode having a thickness of 12.5 nm was deposited and laminated as the anode 5 on an Ag alloy (reflective layer) having a thickness of 190 nm and formed on the substrate 3 composed of a glass plate having a size of 30 mm×30 mm, thereby manufacturing a cell for the organic electroluminescence element for the top emission.

Next, a film made of m-MTDATA [4, 4', 4"-tris(phenyl-m-tolylamino)triphenylamine] was deposited as the hole injecting layer 7a so as to have a thickness of 12 nm (at an evaporation rate of 0.2 to 0.4 nm/sec) in an evaporation process.

Next, in Examples 1 and 2, and Comparative Examples 1 to 3, films made of respective materials shown below were deposited as the hole transport layers 7b so as for each of them to have a thickness of 12 nm (at an evaporation rate of 0.2 to 0.4 nm/sec) in the evaporation process. It is noted that the materials represented by the structural formula (1)-1 and the structural formula (2)-1 used in Examples 1 and 2, respectively, are those represented by the general formula (1) and the general formula (2), respectively, and compounds (1) to (3) used in Comparative Examples 1 to 3, respectively, are materials out of the materials represented by the general formula (1) and the general formula (2), respectively. It is noted that the compound (2) used in Comparison Example 2 is mTTA [Tris-(m-terphenylyl)amine]. In addition, the compound (3) used in Comparative Example 3 is α-NPD [N, N'-bis(1-naphthyl)-N, N'-diphenyl[1, 1'-biphenyl]-4, 4'-diamine], and is the compound which is generally used as the hole transport material.

Example 1:
the structural formula (1)-1
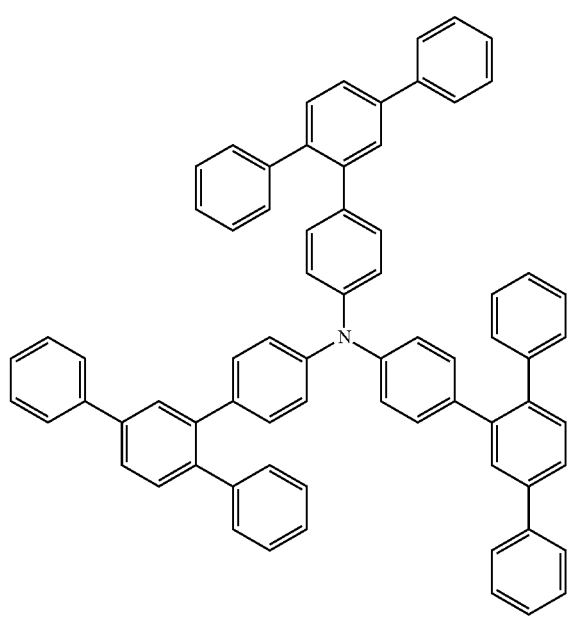
Example 2:
the structural formula (2)-1
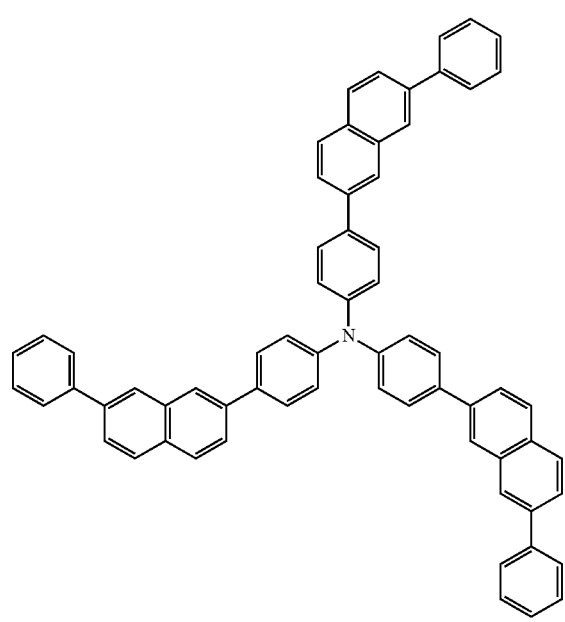
Comparative example 1:
the compound (1)
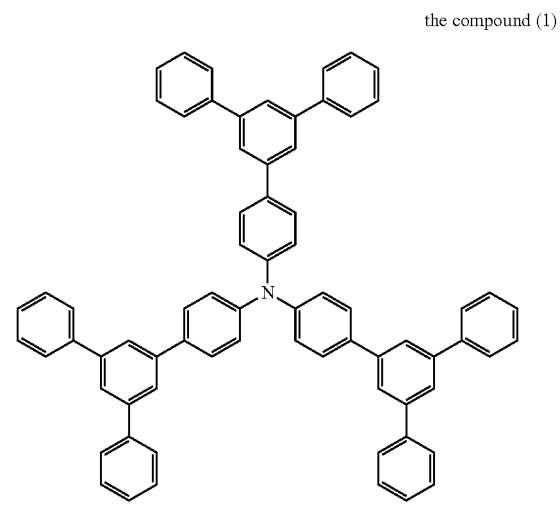
Comparative example 2:
the compound (2)
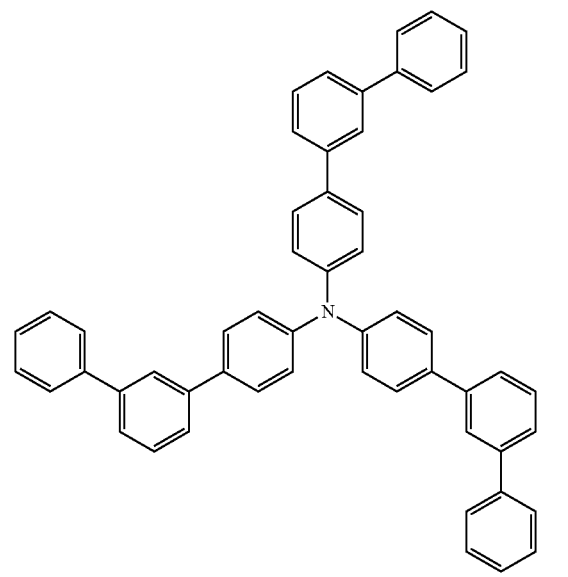
mTTA
Comparative example 3:
the compound (3)
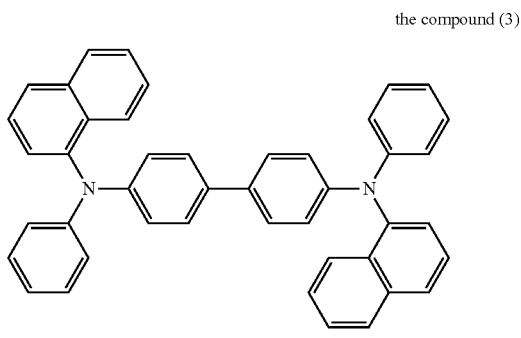
α-NPD
Next, a film which was obtained by doping a host material made of the following compound H1 with a dopant material made of the following compound D1 at a concentration of 5% was deposited as the light emitting layer 7c in the evaporation process so as to have a thickness of 30 nm. In this case, the compound H1 and the compound D1 were formed in a co-evaporation process. It is noted that the compound D1 is a blue luminescent dopant material.

the compound H-1

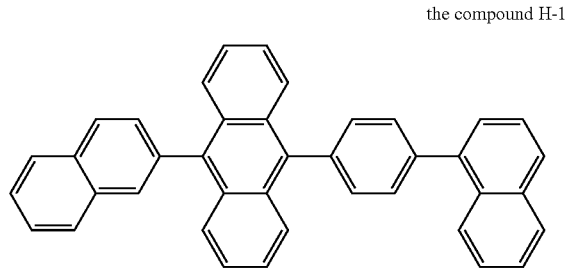

-continued the compound D-1

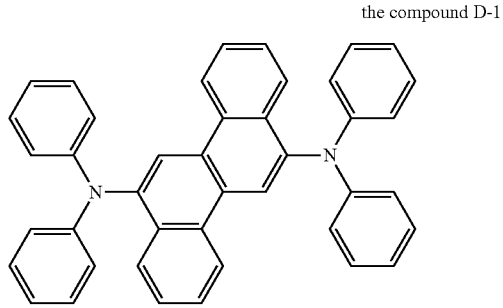

Next, an Alq3 [tris(8-hydroxyquinoline)aluminum] film was deposited as the electron transport layer 7d in the evaporation process so as to have a thickness of 30 nm.

After that, a lithium fluoride was deposited as the cathode interface layer 9 in the evaporation process so as to have a thickness of 1 nm, and also a MgAg film was deposited as the cathode 11 in the evaporation process so as to have a thickness of 12 nm, thereby manufacturing each of the organic electroluminescence elements of Examples 1 and 2, and Comparative Examples 1 to 3.

With regard to the organic electroluminescence elements manufactured in Examples 1 and 2, and Comparative Examples 1 to 3 described above, respectively, a current efficiency (cd/A) in a phase of the driving at a current density of 10 mA/cm² was measured. In addition, a time until an initial luminance of 1 was changed to 0.5 when a constant current driving for a load at the current density of 50 mA/cm² was carried out at 50° C. and at a duty of 25% was measured as a luminance half-life (hour). In addition, the organic electroluminescence elements manufactured in Examples 1 and 2, and Comparative Examples 1 to 3 were heated at 120° C. for one hour. After that, the current efficiency (cd/A) and the luminance half-life (hour) were measured therefor similarly to the above case. The measurement results are shown in TABLE 1.

TABLE 1

| | hole transport layer 7b (material) | before heating | | after heating | |
|---|---|---|---|---|---|
| | | current efficiency (cd/A) | luminance half-life (hour) | current efficiency (cd/A) | luminance half-life (hour) |
| Example 1 | structural formula (1)-1 | 2.3 | 800 | 2.2 | 750 |
| Example 2 | structural formula (2)-1 | 2.2 | 900 | 2.2 | 900 |
| Example 3 | structural formula (1)-22 | 29.0 | 480 | 28.0 | 450 |
| Example 4 | structural formula (2)-18 | 27.0 | 500 | 25.0 | 480 |
| Comparative Example 1 | compound (1) | 2.2 | 600 | 1.5 | 300 |
| Comparative Example 2 | compound (2) | 2.1 | 800 | 0.3 | 100 |
| Comparative Example 3 | compound (3) | 1.0 | 600 | 0.1 | 100 |
| Comparative Example 4 | compound (4) | 26.0 | 480 | 2.0 | 220 |
| Comparative Example 5 | compound (5) | 25.0 | 200 | 22.0 | 150 |
| Comparative Example 6 | compound (6) [compound (2)] | 23.0 | 200 | 1.5 | 150 |

It was confirmed that as shown in TABLE 1, the reduction of the current efficiency and the luminance half-life after the heating are suppressed smaller in each of the organic electroluminescence elements of Examples 1 and 2 in which the hole transport layers 7b were made of the materials represented by the structural formula (1)-1 and the structural formula (2)-1, respectively, than in each of the organic electroluminescence elements of Comparative Examples 1 to 3.

Here, the material represented by the structural formula (1)-1 and used in Example 1 is a phenyl substitution product of the compound (2) [mTTA: Tris-(m-terphenylyl) amine] used in Comparative Example 2. In addition, the material represented by the structural formula (2)-1 and used in Example 2 is a benzene ring condensation product of the compound (2) used in Comparative Example 2. It was understood from this that the large enhancement is recognized in the efficiency/life characteristics by the phenyl substitution and the benzene ring fused ring of the amine system material [mTTA of the compound (2)] which has been known in related art as the material composing the organic light emitting functional layer.

On the other hand, the compound (1) used in Comparative Example 1 is also the phenyl substitution product of the compound (2) used in Comparative Example 2. However, in the organic electroluminescence element in Comparative Example 1, the current efficiency after the heating is reduced by 32% with respect to Example 1, and the luminance half-life is also reduced by 57% with respect to Example 1. It is clear from this that the enhancement of the heat resistance property is not expected in the case of using the phenyl substitution and the benzene ring fused ring of the simple compound (2) [mTTA].

It was confirmed from the above that the enhancement of the luminous efficiency, and the lengthening of the life are realized for the organic electroluminescence element under the high temperature condition by applying the present embodiment.

It is noted that with regard to one of indices, a glass transition point (Tg) of a constituent material gives an indication of the enhancement of the heat resistance property of the element in some cases. This technique, for example, is described in WO 05/063684, and a non-patent document of Shirota, Y. et al, Chem. Rev. 2007, 107, p. 953.

Even in the design of the constituent material of the organic light emitting material layer in the present embodiment, the glass transition point (Tg) is consulted for one index for the enhancement of the heat resistance property. With regard to an example thereof, the material represented by the structural formula (2)-1 has a glass transition point (Tg) which is about 20° C. higher than that of the compound (2).

Examples 3 and 4 Comparative Examples 4 to 6

The organic electroluminescence element 1' having the structure described with reference to FIG. 2 was manufactured in the manner which will be described below.

Firstly, an ITO transparent electrode having a thickness of 100 nm was formed as the anode 5 on the substrate 3 composed of a glass plate having a size of 30 mm×30 mm, thereby manufacturing a cell for an organic electroluminescence element for top emission.

Next, the substrate 3 having the anode 5 formed thereon was fixed to a substrate holder in an evaporation system, and an evaporation mask was disposed close to the substrate 3. Evaporation materials were placed in respective boats, and the boats were then mounted to predetermined electrodes of the evaporation system, respectively. Under this state, a pressure in an evaporation vessel was reduced to $1.4 \times 10^{-4}$ Pa and the organic layers and the cathode were deposited in order on the anode 5 in the evaporation process in the manner which will be described below.

Firstly, in Examples 3 and 4, and Comparative Examples 4 to 6, films made of the respective materials represented by the following structural formulas were deposited as the hole transport layer 7b so as for each of them to have a thickness of 30 nm. It is noted that the materials represented by the structural formulas (1)-22 and (2)-18 used in Examples 3 and 4, respectively, are the materials represented by the general formulas (1) and (2), respectively, and the compounds (2) to (6) used in Comparative Examples 4 to 6 are the materials out of those represented by the general formulas (1) and (2), respectively. However, the compound (6) is the same as the compound (2) used in Comparative Example 2, i.e., mTTA [Tris-(m-terphenylyl)amine].

Example 3:

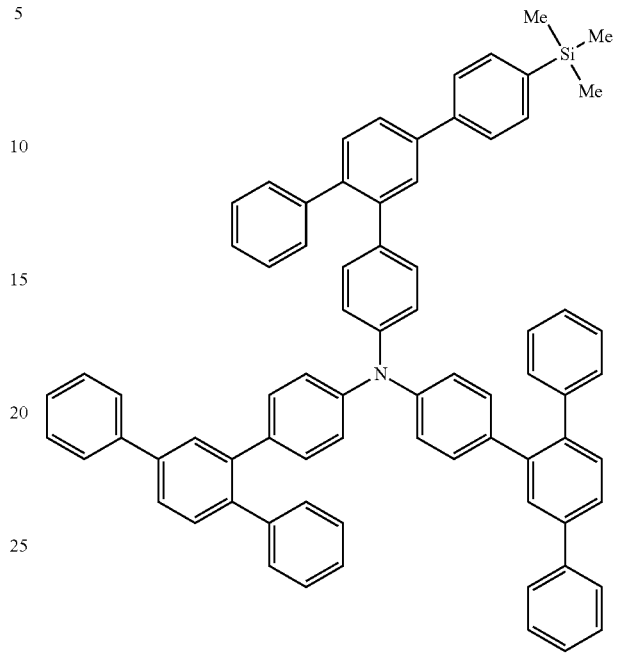

the structural formula (1)-22

Example 4:

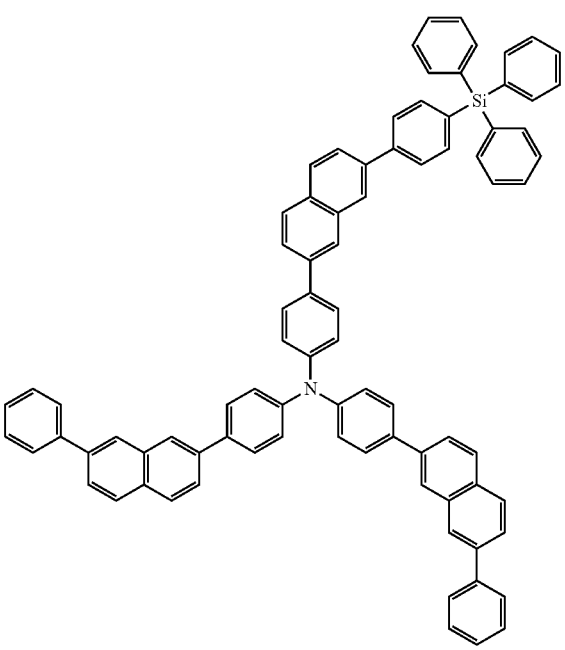

the structural formula (2)-18

Comparative example 4:

the compound (4)

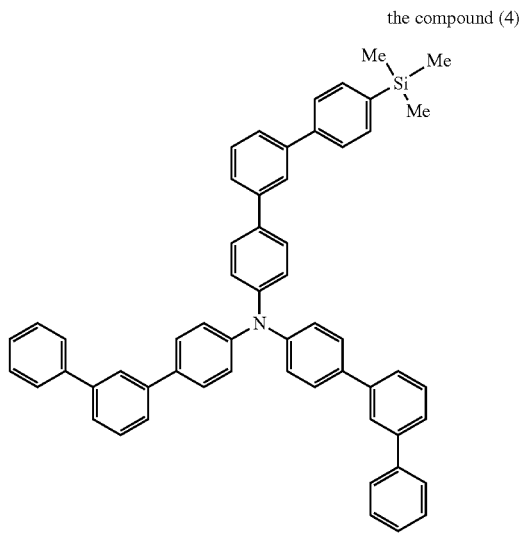

Comparative example 6:

the compound (6)

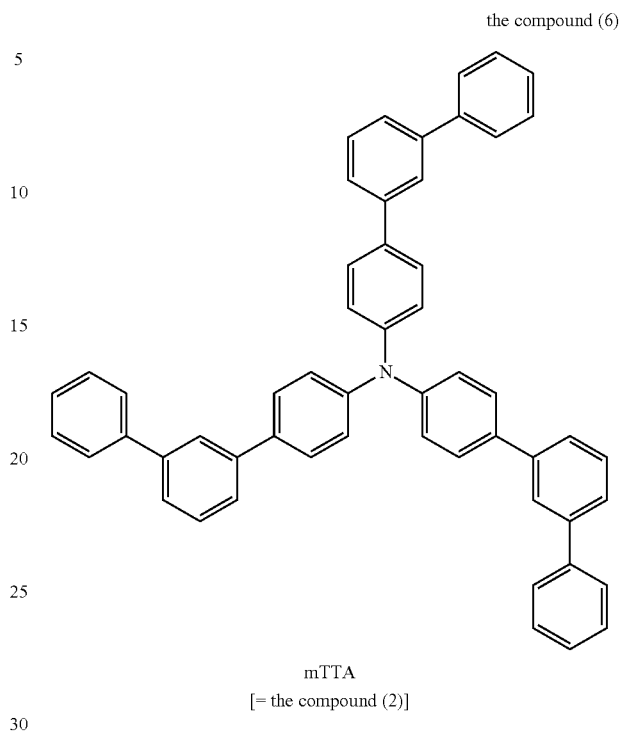

mTTA
[= the compound (2)]

Next, a film which was obtained by doping a host material made of the following compound H2 with a dopant material made of the following compound D2 at a concentration of 10% was deposited as the light emitting layer 7c in the evaporation process so as to have a thickness of 30 nm. It is noted that the compound H2 is 4, 4'-N, N'-dicarbazole-biphenyl (CBP), and the dopant material made of the compound D2 is an iridium complex having the phosphorescence luminescence.

Comparative example 5:

the compound (5)

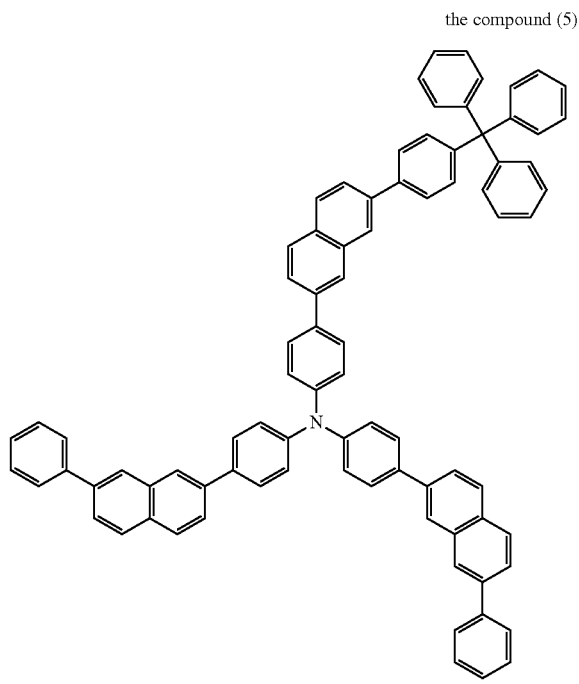

the compound H-2 the compound D-2

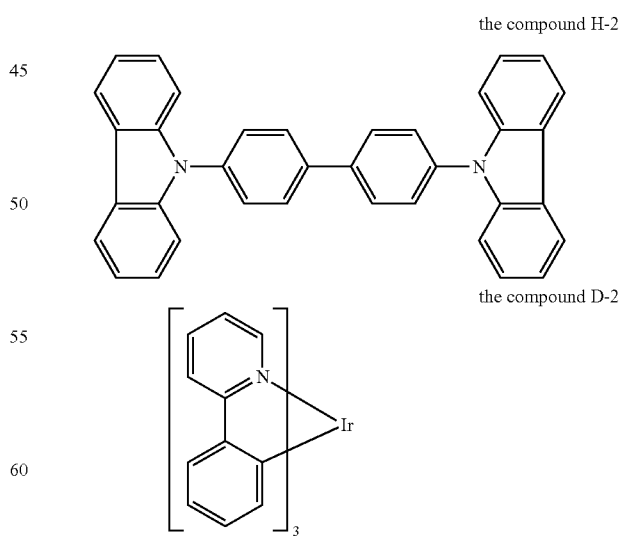

After that, the following compound HBL [2, 9-dimethyl-4, 7-diphenyl-1, 10-phenanthroline(BCP)] was deposited as the hole blocking layer 7d' so as to have a thickness of 10 nm.

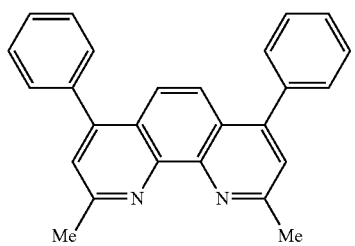

the compound HB

Next, a 8-quinolinol aluminum complex (Alq3) was deposited as the electron transport layer 7d so as to have a thickness of 150 nm.

After that, the formation of the cathode interface layer 9 was omitted, and a MgAg film was deposited as the anode 11 in the evaporation process so as to have a thickness of 12 nm. In this case, magnesium (Mg) and silver (Ag) were deposited at a film deposition rate of 8:2 in the co-evaporation process. The organic electroluminescence elements of Examples 3 and 4, and Comparative Examples 4 to 6 were manufactured in the manner described above.

With regard to each of the organic electroluminescence elements manufactured in Examples 3 and 4, and Comparative Examples 4 to 6, respectively, a forward bias D.C. voltage was applied thereto under a nitrogen ambient, thereby evaluating the light emitting characteristics. The emission color was green, and as a result of carrying out the spectroscopic measurement, a spectrum was obtained which had an emission peak in the vicinity of 520 nm.

In addition, with regard to these organic electroluminescence elements, the current efficiency (cd/A) in the phase of the driving at the current density of 10 mA/cm$^2$ was measured. In addition, a time until an initial luminance of 1 is changed to 0.5 when a constant current driving for a load at the current density of 50 mA/cm$^2$ was carried out at 50° C. and at a duty of 25% was measured as a luminance half-life (hour). In addition, the organic electroluminescence elements manufactured in Examples 3 and 4, and Comparative Examples 4 to 6 were heated at 120° C. for one hour. After that, the current efficiency (cd/A) and the luminance half-life (hour) were measured therefor similarly to the above case. The measurement results are shown together with Examples 1 and 2, and Comparative Examples 1 to 3 in TABLE 1.

It was confirmed that as shown in TABLE 1, the reduction of the current efficiency and the luminance half-life after the heating are suppressed smaller in each of the organic electroluminescence element of Examples 3 and 4 in which the hole transport layers 7b were made of the materials represented by the structural formula (1)-22 and the structural formula (2)-18, respectively, than in each of the organic electroluminescence element of Comparative Examples 4 to 6.

Here, the material represented by the structural formula (1)-22 and used in Example 3 is a phenyl substitution product of the compound (6) [mTTA: Tris-(m-terphenylyl)amine=the compound (2)], and also is a Si substitution product. In addition, the compound (4) used in Comparative example 4 is the Si substitution product of the compound (6) used in Comparative Example 6. However, in the organic electroluminescence element of Comparative example 4, the current efficiency after the heating is reduced from that before the heating by about 1/10, and the luminance half-life is also reduced from that before the heating by 54%. In a word, it was found out that when the organic compound group of the 14-th group element heavier than carbon is merely substituted for a part of the amine system material [mTTA in the compound (6)] which has been known in related art as the material composing the organic light emitting functional layer, the reduction of the element life caused by the heating for the element is unable to be suppressed. It was found out from this that the organic compound group of the 14-th group element heavier than carbon, and the phenyl group are both substituted in a suitable substitution position for mTTA, thereby largely enhancing the efficiency/life characteristics after the heating of the organic electroluminescence element.

In addition, the material represented by the structural formula (2)-18 and used in Example 4 is the Si compound group substitution product of the benzene ring condensation product of the compound (6) [mTTA: Tris-(m-terphenylyl)amine] used in Comparative Example 6. The compound (5) of Comparative Example 5 is the triphenylmethyl group substitution product of the benzene ring condensation product of the compound (6) used in the Comparative Example 6. Since the organic electroluminescence element of Comparative Example 5 is the benzene ring condensation product of the compound (6), the reduction of each of the current efficiency and the luminance half-life after the heating is not so large. However, the original luminance half-life itself before the heating is in the same range as that in Comparative Example 6, and is only about 40% of that in Example 4. From this, it was found out that the organic compound group of the 14-th group element heavier than carbon is substituted in a suitable substitution position for mTTA, thereby largely enhancing the luminance half-life of the organic electroluminescence element.

The present application contains subject matter related to that disclosed in Japanese Priority Patent Application JP 2009-248573 filed in the Japan Patent Office on Oct. 29, 2009 and Japanese Priority Patent Application JP 2009-008709 filed in the Japan Patent Office on Jan. 19, 2009, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An organic electroluminescence element, comprising:
a pair of electrodes; and
an organic light emitting layer, the organic light emitting layer being a multilayer structure made of an organic material held between said pair of electrodes,
wherein,
the organic material contains at least one of a material represented by the general formula (1), and a material represented by the general formula (2),general formulae (1) and (2) being:

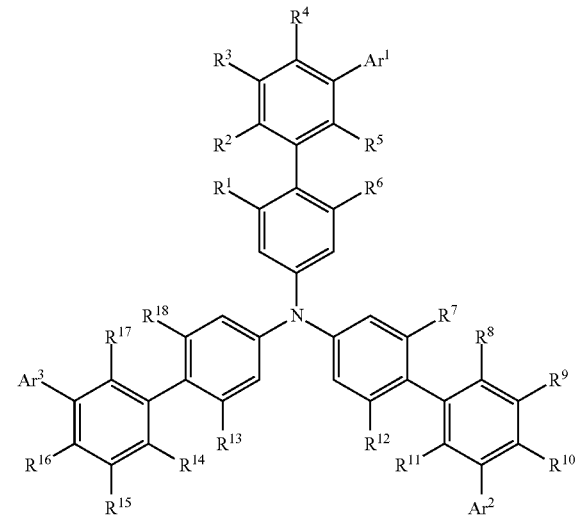

the general formula (1)

where (a) each of $Ar^1$ to $Ar^3$ represent a phenyl group, a naphthyl group, a phenanthrenyl group, and an anthracenyl group and each of the phenyl group, the naphthyl group, the phenanthrenyl group, and the anthracenyl group may include an alkyl group having a carbon number of 6 or less or an organic compound group of 14-th group elements each heavier than carbon is adapted to be substituent, and (b) each of $R^1$ to $R^{18}$ represent a hydrogen, an alkyl group having a carbon number of 6 or less or a phenyl group including an alkyl group having the carbon number of 6 or less as a substituent, and at least one of $R^2$ and $R^5$, and $R^8$ and $R^{11}$ is not hydrogen, and the general formula (2)

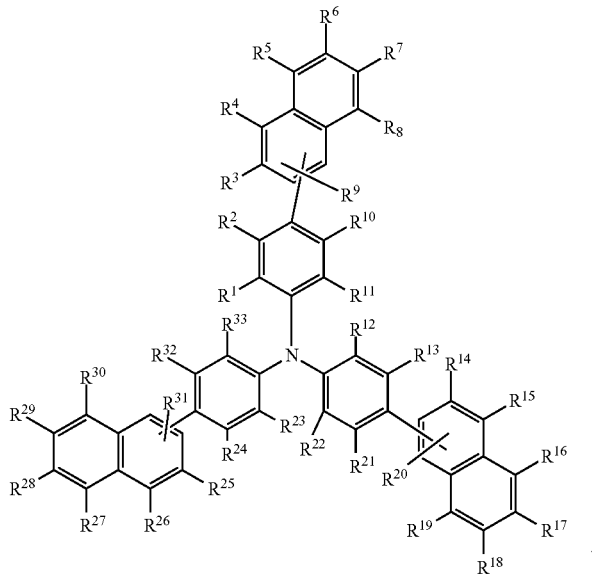

where (a) each of $R^1$ to $R^{33}$ represent a hydrogen, an alkyl group having a carbon number of 6 or less, a phenyl group, a naphthyl group, a phenanthrenyl group, and an anthracenyl group and where each of the phenyl group, the naphthyl group, the phenanthrenyl group, and the anthracenyl group may include an alkyl group having a carbon number of 6 or less or an organic compound group of 14-th group elements each heavier than carbon as a substituent, (b) at least one of $R^9$ $R^{20}$ or $R^{31}$ represents β-H, where the β-H is attached at the β position of a function group, and (c) at least one of $R^4$, $R^{15}$ or $R^{26}$ represents hydrogen or an alkyl group having the carbon number of 6 or less.

2. The organic electroluminescence element according to claim 1, wherein said material represented by the general formula (2) is a compound represented by the structural formula (2)-1:

the structural formula (2)-1

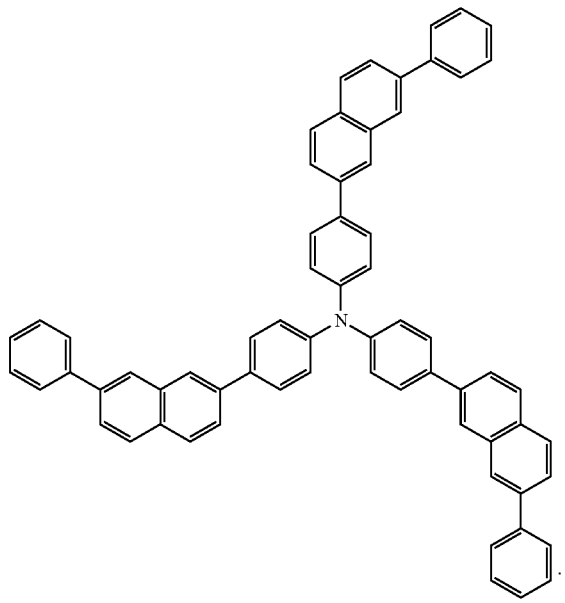

3. The organic electroluminescence element according to claim 1, wherein said material represented by the general formula (2) is a compound represented by the structural formula (2)-18:

the structural formula (2)-18

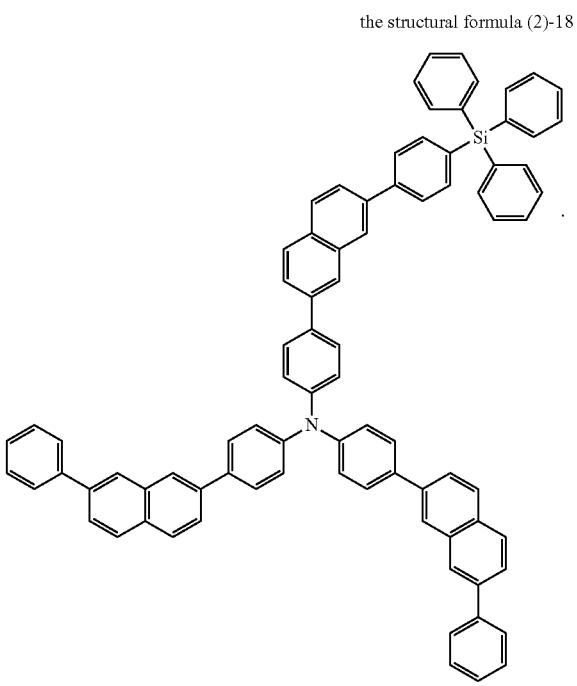 [SMILES: c1ccc(-c2ccc3ccc(-c4ccc(N(c5ccc(-c6ccc7ccc(-c8ccccc8)cc7c6)cc5)c5ccc(-c6ccc7ccc(-c8ccc([Si](c9ccccc9)(c9ccccc9)c9ccccc9)cc8)cc7c6)cc5)cc4)cc3c2)cc1]

4. The organic electroluminescence element according to claim 1, wherein the organic light emitting includes a hole transport layer, and the hole transport layer includes said material represented by the general formula (1) and said material represented by the general formula (2).

5. An organic electroluminescence element comprising:

a pair of electrodes; and an organic light emitting layer, the organic light emitting layer being a multilayer structure made of an organic material between said pair of electrodes, wherein, the organic material contains at least one of a material represented by a structural formula (1)-1, the structural formula (1)-1 being:

the structural formula (1)-1

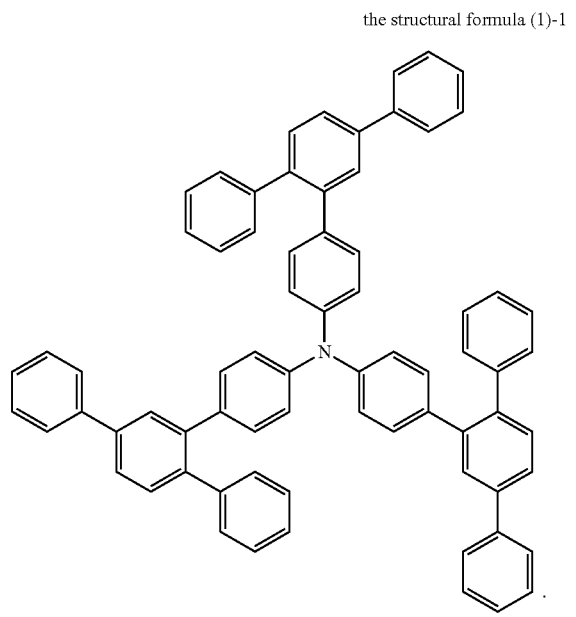 [SMILES: c1ccc(-c2ccc(-c3ccccc3)c(-c3ccc(N(c4ccc(-c5cc(-c6ccccc6)ccc5-c5ccccc5)cc4)c4ccc(-c5cc(-c6ccccc6)ccc5-c5ccccc5)cc4)cc3)c2)cc1]

6. An organic electroluminescence element comprising:

a pair of electrodes; and an organic light emitting layer, the organic light emitting layer being a multilayer structure made of an organic material between said pair of electrodes, wherein, the organic material contains at least one of a material represented by a structural formula (1)-22, the structural formula (1)-22 being:

the structural formula (1)-22

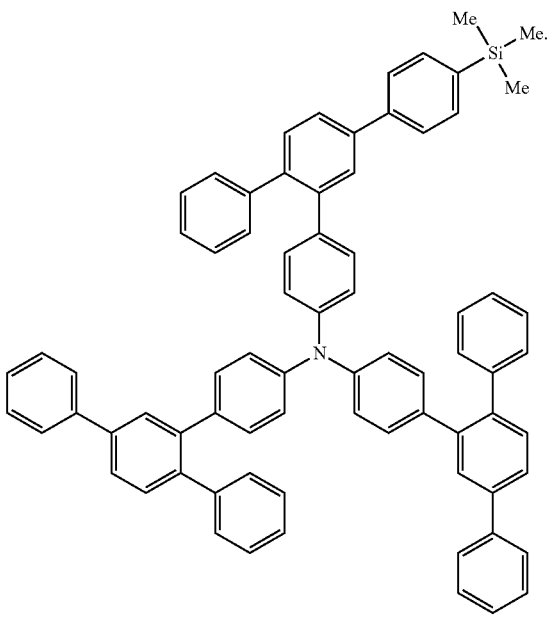

* * * * *